(12) United States Patent
Sarna et al.

(10) Patent No.: US 12,635,687 B2
(45) Date of Patent: May 26, 2026

(54) AQUEOUS HOP EXTRACTS AND THEIR USE AS ANTIMICROBIAL AGENTS

(71) Applicant: Nature Recombined Sciences Inc., West Vancouver (CA)

(72) Inventors: Leonard Sarna, West Vancouver (CA); Kian-Guan Lim, West Vancouver (CA); Mingyang Sun, West Vancouver (CA); Silvia Cardona, West Vancouver (CA); John Sorensen, West Vancouver (CA); Anna Motnenko, West Vancouver (CA)

(73) Assignee: Nature Recombined Sciences Inc., West Vancouver (CA)

( * ) Notice: Subject to any disclaimer, the term of this patent is extended or adjusted under 35 U.S.C. 154(b) by 0 days.

(21) Appl. No.: 18/733,167

(22) Filed: Jun. 4, 2024

(65) Prior Publication Data

US 2025/0017201 A1     Jan. 16, 2025

Related U.S. Application Data

(62) Division of application No. 18/158,077, filed on Jan. 23, 2023, now Pat. No. 12,035,710.

(60) Provisional application No. 63/398,324, filed on Aug. 16, 2022, provisional application No. 63/355,184, filed on Jun. 24, 2022, provisional application No. 63/301,582, filed on Jan. 21, 2022.

(51) Int. Cl.

| | |
|---|---|
| *A01N 25/04* | (2006.01) |
| *A01N 65/08* | (2009.01) |
| *A01P 1/00* | (2006.01) |
| *A61K 36/185* | (2006.01) |

(52) U.S. Cl.
CPC ............. *A01N 25/04* (2013.01); *A01N 65/08* (2013.01); *A01P 1/00* (2021.08); *A61K 36/3486* (2024.05)

(58) Field of Classification Search
None
See application file for complete search history.

(56) References Cited

U.S. PATENT DOCUMENTS

| | | | |
|---|---|---|---|
| 5,750,179 | A | 5/1998 | Guzinski et al. |
| 6,547,971 | B2 | 4/2003 | Breen et al. |
| 7,078,062 | B2 | 7/2006 | Haas |
| 2008/0003190 | A1 | 1/2008 | Wille |
| 2009/0104288 | A1 | 4/2009 | Probasco |
| 2015/0366215 | A1 | 12/2015 | Probasco et al. |
| 2019/0343126 | A1 | 11/2019 | Gaur et al. |
| 2020/0048590 | A1 | 2/2020 | Wolinska |

FOREIGN PATENT DOCUMENTS

| | | | | |
|---|---|---|---|---|
| CA | 3043388 | 11/2019 | | |
| EP | 2601841 | 6/2013 | | |
| WO | WO-2018073384 A1 * | 4/2018 | ............... | C12C 3/08 |

OTHER PUBLICATIONS

Weber et al. (Molecules, 2019, 24(2), 223) (Year: 2019).*
Rusher (https://web.archive.org/web/20201112030117/https://brulosophy.com/2019/09/02/whole-cone-vs-pellet-hops-exbeeriment-results/) (Year: 2011).*
Tronina et al. (Molecules, 2020, 25(18), 4201) (Year: 2020).*
Blaxland et al. (Archaea, 2021, Article ID 5510063, 5 pages) (Year: 2021).*
Arruda et al. (LWT—Food Science and Tech., 2021, 141, 110905).*
Hrncic, M.K. et al. "Hop Compounds: Extraction Techniques, Chemical Analyses, Antioxidative, Antimicrobial, and Anticarcinogenic Effects", Nutrients, Jan. 24, 2019, 11(2), 257 (pp. 1-37), doi:10.3390/nul11020257, ISSN: 2072-6643.
Fahle A. et al. "Antibacterial effects of biologically active ingredients in hop provide promising options to fight infections by pathogens including multidrug resistant bacteria", Eur J Microbiol Immunol (Bp), Apr. 13, 2022, vol. 12, No. 1, pp. 22-30, ISSN:20628633.
Helmja K. et al. "Bioactive components of the hop strobilus: Comparison of different extraction methods by capillary electrophoretic and chromatographic methods", Journal of Chromatography A, Jul. 6, 2007, vol. 1155, pp. 222-229, ISSN:0021-9673.
Guo et al. "Antimicrobial Activity and Proposed Action Mechanism of Linalool Against Pseudomonas Fluerescens" Frontiers in Microbiology, Published Jan. 28, 2021, vol. 12, Article 562094, pp. 1-11.
Elke Genersch, "American Foulbrood in Honeybees and its Causative Agent, Paenibacillus Larvae", Journal of Invertebrate Pathology 103 (2010) S10-S19.
DeGrandi-Hoffman er al. "The Effects of Beta Acids from Hops (*Humulus lupulus*) on Mortality of Varroa Destructor (*Acari: Varroidae*)", Springer, Published online Jul. 6, 2012, pp. 407-421 DOI 10.1007/s10493-012-9593-2.
Aydin et al. "Insecticidal Effects of Extracts of Humulus lupulus (*hops*) L. Cone and its Principal Component, Xanthohumol", Bulletin of Entomological Research (2017) 107, pp. 543-579, doi:10.10174/S0007485317000256.
Stompor et al. "Insect Antifeedant Potential of Xanthohumol, and Their Derivatives", Journal of Agricultural and Food Chemistry 2015, 63, pp. 6749-6756, DOI:10.1021/acs.jafc.5b02025.
Paventi et al. Biological Activity of *Humulus lupulus* (L.) Essential Oil and its Main Components Against *Sitophilus granarius* (L.), Biomolecules 2020, 10, 1108, published Jul. 25, 2020; doi:10.3390/biom10081108, pp. 1-16.

(Continued)

*Primary Examiner* — Erin E Hirt
(74) *Attorney, Agent, or Firm* — Michael R Williams; Ryan W Dupuis; Ade & Company Inc.

(57) ABSTRACT

Described herein is the preparation of an aqueous hop extract and a boiling water hop extract prepared from dried hop cones that were ground prior to extraction. As discussed below, extracts were prepared from a number of different hop varieties and were tested against a number of clinically relevant bacterial strains. As discussed herein, surprisingly, the boiling water extract showed greater antibacterial activity than the aqueous extract.

6 Claims, No Drawings

(56) References Cited

OTHER PUBLICATIONS

Jackowski et al., "Antifeedant Activity of Xanthohumol and Supercritical Carbon Dioxide Extract of Spent Hops Against Stored Product Pests", Bulletin of Entomological Research (2015) 105, pp. 456-461, doi: 10.1017/S0007485315000255.

Garrido-Bailon et al. "The Prevalence of the Honeybee Brood Pathogens Ascosphaera apis, Paenibacillus larvae and Melissococcus plutonius in Spanish Apiaries Determined with a New Multiplex PCR Assay", Microbial Biotechnology published by John Wiley & Sons Ltd and Society for Applied Microbiology; pp. 731-739.

Fahle et al. "Antibacterial Effects of Biologically Active Ingredients in Hop Provide Promising Options to Fight Infections by Pathogens Including Multi-drug Resistant Bacteria", European Journal of Microbiology and Immunology 12 (2022) 1, pp. 22-30; DOI:10. 1556/1886.2022.00006.

Funfhaus et al. "Swarming Motility and Biofilm Formation of Paenibacillus larvae, the Etiological Agent of American Foulbrood of Honey Bees (*Apis mellifera*)", Scientific Reports, published online Jun. 11, 2018 (8:8840), pp. 1-12, DOI:10.1038/s41598-018-27193-8.

Guo et al., "Antibacterial Activity and Mechanism of Linalool Against Shewanella putrefaciens", Molecules 2021, 26, 245; DOI:10. 3390/molecules26010245, pp. 2-17.

Iglesias A et al: "Valorization of hop leaves for Development of eco-friendly bee pesticides", Apidologie, Arbeitsgemeinschaft der Institute fuer Bienenforschung, Celle, De, vol. 52, No. 1, Sep. 25, 2020, pp. 186-198; ISSN: 0044-8435, DOI: 10.1007/S13592-020-00808-8.

* cited by examiner

AQUEOUS HOP EXTRACTS AND THEIR USE AS ANTIMICROBIAL AGENTS

PRIOR APPLICATION INFORMATION

The instant application is a divisional application of U.S. Ser. No. 18/158,077, filed Jan. 23, 2023, which claimed the benefit of (i) U.S. Provisional Patent Application 63/301,582, filed Jan. 21, 2022 and entitled "AQUEOUS HOP EXTRACTS AND THEIR USE AS ANTIMICROBIAL AGENTS", the entire contents of which are incorporated herein by reference for all purposes; (ii) U.S. Provisional Patent Application 63/355,184, filed Jun. 24, 2022 and entitled "AQUEOUS HOP EXTRACTS AND THEIR USE AS ANTIMICROBIAL AGENTS", the entire contents of which are incorporated herein by reference for all purposes; and (iii) U.S. Provisional Patent Application 63/398,324, filed Aug. 16, 2022 and entitled "USE OF HOP EXTRACTS AGAINST PAENIBACILLUS LARVAE", the entire contents of which are incorporated herein by reference for all purposes.

BACKGROUND OF THE INVENTION

Antimicrobial resistance is an increasingly serious threat to global public health that requires immediate action across all sectors of government and society. While the repertoire of pharmaceutically prescribed antibiotics is large, bacteria continue to evolve and evade the antimicrobial activity of commercial antibiotics. This has led to the development of antibiotic resistance.

The development of resistant strains of bacteria is a natural phenomenon that occurs when microorganisms replicate themselves erroneously or when resistant traits are exchanged between them. Antimicrobial resistance can be genetically based. For example, resistance can be mediated by the acquisition of extrachromosomal genetic elements containing genes that confer resistance to certain antibiotics. Examples of such elements include plasmids, transposable genetic elements, and genomic islands, which can be transferred between bacteria through horizontal gene transfer.

The use and misuse of antimicrobial drugs accelerates the emergence of drug-resistant strains. Poor infection control practices, inadequate sanitary conditions and inappropriate food handling encourage the further spread of antimicrobial resistance.

The high proportion of antibiotic resistance in bacteria that cause common infections, e.g., urinary tract infections, pneumonia, and infections of the blood is cause for concern as presently approved antibiotic agents are less effective at treating such infections. For example, an important objective of antibiotic R&D today is to find chemical agents that are effective for the treatment of for example methicillin-resistant *Staphylococcus aureus* (MRSA), which is responsible for a majority of bacterial infection in hospitals, the elderly, infants and persons with compromised immunity.

*Varroa destructor* and *V. jacobsoni* are external parasitic mites that attack and feed on the honey bees *Apis cerana* and *Apis mellifera*. The disease caused by the mites is called varroosis. The Varroa mite can reproduce only in a honey bee colony. It attaches to the body of the bee and weakens the bee by sucking fat bodies. The species is a vector for at least five debilitating bee viruses, including RNA viruses such as the deformed wing virus (DWV).

The Western honey bee *Apis mellifera* is a generalist pollinator and managed colonies of *A. mellifera* are widely used in global agriculture for the pollination of many crops and fruit grown in the open field. In addition, *A. mellifera* also pollinates numerous wild flowers thus contributing to biodiversity in natural ecosystems.

American Foulbrood is a worldwide distributed, fatal disease of the brood of the Western honey bee (*Apis mellifera*). The causative agent of this fatal brood disease is the Gram-positive, spore-forming bacterium *Paenibacillus larvae*, which can be classified into four different genotypes (ERIC I-IV), with ERIC I and II being the ones isolated from contemporary AFB outbreaks. Accordingly, among the pathogens posing the most serious threats to honey bees is *Paenibacillus larvae*. *P. larvae* only infects bee larvae, hence, AFB only affects the bee brood, but still the disease is able to kill entire colonies if left untreated. AFB is highly contagious and spreads quite fast within and between honey bee colonies and apiaries. Specifically, under normal beekeeping conditions, AFB are highly contagious since spread of the disease is facilitated by exchanging hive and bee material between colonies, managing numerous hives in a confined area and the trading of queens, colonies ("package bees") and honey. Burning of colonies and contaminated hive material are widely considered the only workable control measure for diseased colonies whereas the shook swarm method (shaking the bees onto new comb foundation and destroying the infected comb) is sometimes applied to sanitize infected, although not yet clinically diseased, colonies.

AFB only affects the larval stages of honeybees. The extremely tenacious endospores are the only infectious form of this organism. The spores are infectious only for larvae; adult bees do not become infected upon ingestion of *P. larvae* spores. Larvae are most susceptible to infection during the early larval stages, i.e. 12-36 h after egg hatching. During this time window, the oral uptake of a dose of about ten spores or fewer via contaminated larval food is sufficient to successfully initiate a fatal infection if the spores enter vegetative growth stage following infection.

Many bacterial species are able to switch between planktonic growth and biofilm formation. The broadest definition of a biofilm is that it represents cooperatively acting microorganisms forming cell clusters which are held together and protected from adverse external influence by an extracellular matrix secreted by the members of the biofilm. This matrix is a characteristic of bacterial biofilms and consists of exopolysaccharides, secreted proteins, amyloid fibres, and sometimes nucleic acids. Biofilms are of tremendous relevance because they not only protect bacteria from the host's immune system but also render them refractory against antimicrobial treatment. Bacterially produced extracellular matrix is a hallmark and prerequisite of biofilms and genes encoding exopolysaccharide biosynthesis proteins have been annotated in the genome of *P. larvae* (ERIC I: GenBank ETK30098.1; ERIC II: GenBank AHD06625.1). Furthermore, the slimy consistence of the bacterial mass which remains after total degradation of larval cadaver points to biofilm formation by *P. larvae* at least at the end of its lifecycle.

Specifically, American foulbrood disease occurs as newly germinated *P. larvae* cells proliferate in first or second instar larvae. Once germinated, *P. larvae* cells are able to proliferate in the incoming larval diet and larval hemolymph. Furthermore, *P. larvae* produces toxins and cytolysins similar to other pathogenic bacteria which aid in killing the host. An important step for AFB disease development is breaching of the midgut by *P. larvae* cells. Proteases, collagenases, chitinase, and toxins are believed to allow *P. larvae* to breach the midgut via degradation of connective tissue.

Extreme bacteremia causes the death of larvae several days after *P. larvae* spore infection. After the nutrients in honey bee larvae are depleted, *P. larvae* cells sporulate forming billions of spores that are distributed in the colony allowing the disease to continue.

European foulbrood (abbreviated EFB) is a bacterial disease that effects honey bee larvae before the capped stage. European foulbrood disease is characterized by dead and dying larvae which can appear curled upwards, brown or yellow, melted, and/or dried out and rubbery. The causative bacteria, *Melissococcus plutonius* is ingested by honey bee larvae after which the bacterium competes for food inside the larvae. If the bacteria out-competes the larva, the larva will die before the cell is capped. Yearly reoccurrence of EFB from contaminated combs and equipment can occur. The bacteria that causes EFB does not produce spores, but combs contaminated with the bacteria can still reinfect honey bees in subsequent years.

SUMMARY OF THE INVENTION

According to an aspect of the invention, there is provided a method of preparing an anti-microbial composition comprising grinding a quantity of hop cones from the hop plant suspending the ground hop cones in water, boiling the suspension for at least about 15, 20 or 30 minutes and recovering the supernatant.

According to an aspect of the invention, there is provided a method of preparing an anti-*P. larvae* and/or anti-*M. plutonius* and/or anti-Varroa mite composition comprising grinding a quantity of hop cones from the hop plant suspending the ground hop cones in water, boiling the suspension for at least about 15, 20 or 30 minutes and recovering the supernatant.

According to an aspect of the invention, there is provided a method for treating, preventing or reducing the severity of American Foulbrood, European Foulbrood, a *M. plutonius* infection, a *P. larvae* infection and/or a *Varroa* mite infestation of a bee hive comprising: grinding a quantity of hop cones from hop plants, suspending the ground hop cones in water, boiling the suspension for at least about 15, 20 or 30 minutes, recovering the supernatant, thereby providing a hop water extract or a boiled water hop extract, applying the hop water extract or the boiled water hop extract to a honeybee hive.

According to another aspect of the invention, there is provided a method for treating, preventing or reducing the severity of a *P. larvae* infection and/or a *Varroa* mite infestation of a bee hive comprising: grinding a quantity of hop cones from hop plants, suspending the ground hop cones in water, boiling the suspension for at least about 15, 20 or 30 minutes, recovering the supernatant, thereby providing a hop water extract or a boiled water hop extract, applying the hop water extract or the boiled water hop extract to a honeybee hive.

According to another aspect of the invention, there is provided an aqueous hop extract for use as an anti-microbial comprising an effective amount of one or more, two or more, three or more or four or more of the group consisting of: humulene, caryophyllene, myrcene, farnesene, linalool, nerodiol and limolene and/or an effective amount of one or more, two or more, or three of the group consisting of: iso-cohumulone, iso-humulone and iso-adhumulone.

DESCRIPTION OF EMBODIMENTS

Unless defined otherwise, all technical and scientific terms used herein have the same meaning as commonly understood by one of ordinary skill in the art to which the invention belongs. Although methods and materials similar or equivalent to those described herein can be used to practice the present invention, the specification describes methods used to practice the present invention. It is to be understood that the contents of all patents and publications referenced herein are incorporated by reference in their entirety.

Hops (*Humulus lupulus* L.) is known to contain a number of either known or suspected anti-bacterial compounds, including but by no means limited to essential oils, prenyl-flavonoids, phenolic compounds, polyfunctional thiols and bitter acids.

Xanthohumol is the main prenylflavonoid in hops and shows increased solubility as the polarity of organic solvents increase (Aydin et al., 2017, Bulletin of Entomological Research 107: 543-549). However, xanthohumol is converted into the corresponding isomeric prenylflavanone isoxanthohumol during for example the process of brewing beer. Although isoxanthohumol has significantly better solubility than xanthohumol, isoxanthohumol is widely considered to have less "promising" biological properties.

Furthermore, Jackowski et al (2015, Bulletin of Entomological Research 105: 456-461) demonstrated that crude spent hops had a stronger insect deterrent activity than pure xanthohumol.

For example, the essential oils include but are by no means limited to monoterpenes and sesquiterpenes such as for example humulene, bisabolene, caryophyllene, farnesene, elemene and structurally related compounds.

Paventi et al (2020, Biomolecules 10: 1108) demonstrated that $\alpha$-humulene, $\alpha$-myrcene and $\beta$-caryophyllene had activity against different strains of Gram-positive and Gram-negative bacteria. However, this activity was found in the essential oil fraction of hops, which is known to have different properties from for example water and ethanol extracts. For example, PubChem states that myrcene is insoluble in water. As such, one of skill in the art would expect the essential oil fraction(s) to at best form an emulsion but would not mix with water.

For example, the essential oils include but are by no means limited to monoterpenes and sesquiterpenes such as for example humulene, bisabolene, caryophyllene, farnesene, elemene and structurally related compounds.

Bitter acids include $\alpha$-acids, $\beta$-acids and iso-$\alpha$-acids such as for example humulones, iso-humulones, cohumulones, iso-cohumulones, adhumulones, iso-adhumulones, colupulone and the like.

Phenolic compounds include but are by no means limited to hexosides, dihexosides, pentosides, quinic conjugates and proanthocyanidins.

Polyfunctional thiols include but are by no means limited to 3-sulfanylhexan-1-ol (3SH), 3-sulfanylhexyl acetate (3SHA), 4-methyl-sulfanylpentan-2-one (4MSP), 3-sulfanyl-4-methylpentan-1-ol (3S4MP) and 3-sulfanyl-4-methylpentyl acetate (3S4MPA).

As will be appreciated by one of skill in the art, extracts prepared from hop plants will vary in their composition of these compounds based on the plant part(s) extracted, as well as on the nature of the solvent used and the applied extraction method. For example, hop oil is present in the lupulin gland of the hop cone and which includes terpenoids such as for example $\alpha$-humulene, $\beta$-myrcene, linalool and the like.

While for example humulone, lupulone and xanthohumol have been tested for anti-microbial activity, the compounds have typically been suspended in non-aqueous solvents such as for example ethyl alcohol, propylene glycol and DMSO (Fahle et al., 2022, E J Micro and Immuno 12: 22-30)

As discussed herein, compounds such as xanthohumol, HBAs and the essential oils are understood to not be highly soluble in water. While the solubility of these compounds may be increased in boiling water, it is important to note that the solubility would consequently decrease as the boiling water extract cooled.

Described herein is the preparation of an aqueous hop extract and a boiling water hop extract prepared from dried hop cones that were ground prior to extraction. As discussed below, extracts were prepared from a number of different hop varieties and were tested against a number of clinically relevant bacterial strains. As discussed herein, surprisingly, the boiling water extract showed greater antibacterial activity than a non-boiling water or aqueous extract, suggesting that anti-bacterial agents are being released and/or being modified during or by boiling, especially when boiled for an extended period of time, for example, at least 15, 20 or 30 minutes, which is considerably longer than the boiling time for preparation of for examples teas and the like prepared from parts of the hop plant, as discussed herein.

As will be apparent to one of skill in the art, while extracts prepared from dried hop cones are described herein, based on the fact that hop plants have trichome structures, it is likely that there is similar or comparable activity in the leaves and stems of the hop plant varieties. As such, in some embodiments of the invention, boiling water extracts of other plants parts, for example, hop cones and/or hop leaves and/or hop stems and/or plant roots and/or rhizome are within the scope of the invention. Furthermore, given that it is possible that at least some of the bioactive material is secreted by the hop plants, for example, some anti-bacterial activity may be recovered from the rhizosphere of the plants.

Specifically, hop varieties tested include Brewers Gold; Cascade; Cashmere; Centennial; Challenger; Chinook; Crystal; Galena; Hallertau; Magnum; Northern Brew; Nugget; Saaz; Wild Manitoba hop; and Willamette.

Both extract types were tested against *Bacillus subtilis, Staphylococcus aureus*; Methicillin-resistant *Staphylococcus aureus; Cutibacterium acnes (Propionibacterium acnes); Listeria monocytogenes; Streptococcus pneumoniae; Streptococcus pyogenes.* Vancomycin-resistant *Enterococcus faecium, S. typhimurium, E. coli, P. aeruginosa, S. enterica, S. choleraesius, A. vitis,* and *C. albicans.*

*Bacillus subtilis* is a Gram-positive, catalase-positive bacterium, found in soil and the gastrointestinal tract of ruminants and humans. As known to those of skill in the art, *Bacillus subtilis* is often used as a model system for Gram positive bacteria.

*Staphylococcus aureus* is a Gram-positive, round-shaped bacterium that is a member of the Firmicutes, and it is a usual member of the microbiota of the body, frequently found in the upper respiratory tract and on the skin. Although *S. aureus* usually acts as a commensal of the human microbiota it can also become an opportunistic pathogen, being a common cause of skin infections including abscesses, respiratory infections such as sinusitis, and food poisoning.

Methicillin-resistant *Staphylococcus aureus* resistance to methicillin is mediated via the mec operon, part of the staphylococcal cassette chromosome mec (SCCmec). SCC-mec is a family of mobile genetic elements, which is a major driving force of *S. aureus* evolution. Resistance is conferred by the mecA gene, which codes for an altered penicillin-binding protein that has a lower affinity for binding β-lactams. This allows for resistance to all β-lactam antibiotics, and obviates their clinical use during MRSA infections.

*Cutibacterium acnes* (formerly *Propionibacterium acnes*) is the relatively slow-growing, typically aerotolerant anaerobic, Gram-positive bacterium (rod) linked to the skin condition of acne; it can also cause chronic blepharitis and endophthalmitis. It lives, among other things, primarily on fatty acids in sebum secreted by sebaceous glands in the follicles. It may also be found throughout the gastrointestinal tract.

*Listeria monocytogenes* is a Gram-positive bacterium, and is the species of pathogenic bacteria that causes the infection listeriosis. It can grow and reproduce inside the host's cells and is one of the most virulent foodborne pathogens.

*Streptococcus pneumoniae* or *pneumococcus*, is a Gram-positive, spherical bacteria and resides asymptomatically in healthy carriers typically colonizing the respiratory tract, sinuses, and nasal cavity. However, in susceptible individuals with weaker immune systems, such as the elderly and young children, the bacterium may become pathogenic and spread to other locations to cause disease. It spreads by direct person-to-person contact via respiratory droplets and by auto inoculation in persons carrying the bacteria in their upper respiratory tracts.

*Streptococcus pyogenes* is a species of Gram-positive, aerotolerant bacterium and is an infrequent, but usually pathogenic, part of the skin microbiota.

Vancomycin-resistant *Enterococcus faecium.* are bacterial strains of the genus *Enterococcus* that are resistant to the antibiotic vancomycin. *Enterococcus faecium* is a Gram-positive, alpha-hemolytic or non-hemolytic bacterium It can be commensal in the gastrointestinal tract of humans and animals, but it may also be pathogenic, causing diseases such as neonatal meningitis or endocarditis.

Accordingly, as discussed herein, the aqueous hop extract, the boiling water hop extract and/or anti-bacterial compounds isolated therefrom can be used as or formulated as therapeutics for treating a broad spectrum of Gram-positive bacterial infections in a patient in need of such treatment.

Specifically, as can be seen on review of the accompanying tables, boiling water extracts from all of the hop varieties tested showed significant effectiveness against *B. subtilis, S. aureus*, MRSA, VRE, *L. monocytogenes*, and *C. acnes*. As will be appreciated by one of skill in the art, this indicates that it is a strong prediction that properties against these bacteria is a common feature of aqueous extracts, for example, boiling water hop extracts, prepared as described herein from any and all hop varieties.

As will be appreciated by one of skill in the art, the *S. aureus* and *S. aureus* MRSA data is interesting because this indicates that the hop boiling water extracts are working through a pathway that is independent of the MRSA resistance. Furthermore, this indicates that antibacterial products derived or developed from the boiling water hop extracts can be used against or to prevent infection by or spread of any *S. aureus* strain, without needing to know if it was a resistant strain. As will be appreciated by one of skill in the art, "spread" of the *S. aureus* strain can be "prevented" by reducing viable colony forming units of *S. aureus* on any suitable surface.

Furthermore, the fact that the hop extracts are able to achieve high mortality in the *S. aureus* and *S. aureus* MRSA strains, as shown at least in Tables 3-6, indicates that the boiling water hop extract and/or antibacterial compounds isolated therefrom can be used in pharmaceutical applications specifically for treatment of *S. aureus* infections.

Furthermore, considerable information on the nature of the boiling water hop extract can be determined from close examination of the results, particularly regarding the effectiveness of the different varieties against *Listeria monocytogenes; Streptococcus pyogenes* and Vancomycin-resistant *Enterococcus faecium.*

As will be appreciated by one of skill in the art, these data indicate that the antibacterial activities of the aqueous hop extract and the boiling water hop extract are not caused by a single compound but must be the result of multiple compounds which appear to affect the different Gram-positive bacteria strains in different ways.

As will be appreciated by one of skill in the art, this indicates not only that the anti-bacterial activity of the aqueous hop extract and the boiling water hop extract described herein is multi-factorial, but also that different varieties can contain different levels of these anti-bacterial compounds. As will be appreciated by one of skill in the art, these strain-specific anti-microbials can be identified and then isolated or purified or otherwise concentrated and accordingly used in strain-specific medicaments and products, as discussed herein.

Additional data on individual strains and specific hop varieties can be found in the examples.

While not wishing to be bound to a particular theory or hypothesis, it is known that from for example a historical overview of the antibacterial properties of hop extracts can be found in Published PCT Application WO02/069741, incorporated herein by reference for all purposes, but especially for its disclosure regarding hop plant extracts, it is known that hop plants produce a number of compounds known to have or purported to have antibacterial properties, such as, for example: alpha acids, including but by no means limited to humulone, lupelone, cohumulone and adhumulone; beta acids, including but by no means limited to lupulone, colupulone, and adlupulone; xanthohumol; ferulic acid; hexahydroiso-α-acids (isopropyl, isobutyl, secbutyl); tetrahydroiso-α-acids (isopropyl, isobutyl, secbutyl); and iso-α-acids (isopropyl, isobutyl, secbutyl). For example, hop varieties generally have bitter alph-acid content of 5.0-14.0%, bitter beta acid content of 4.0-10.0% and cohumulone content of 27-40%. However, the anti-bacterial activity of the hop cone extract from the different hop varieties does not show a simple pattern based on alph-acid, bet-acid and/or cohumulone content, as discussed in greater detail herein. While not wishing to be bound to a particular theory or hypothesis, it is believed that other compounds known to be present in hop plants, such as, for example, but by no means limited to, the thiols and their conjugates, other prenylflavonoids flavanones and stilbenes, are providing anti-bacterial activity.

For example, Tables 21 and 22 provide information on the compound percentages of the oil and acid fractions of the aqueous extract for Willamette (W1), Nugget (N1), Galena (G1) and Magnum (M1). Note that the compounds in Table 21 were only detectable when the extract was concentrated and are thus very dilute in the aqueous extract, although, as discussed below, these compounds are present in sufficient amounts such that there is antimicrobial activity. Accordingly, the terpene results are based on a concentrated sample of each extract and are expressed in relative amounts, that is the ratio of the analyte present to the most abundant terpene (Nerolidol 2), set arbitrarily to 100%. By way of reference, prior to being set at 100%, the percentage of Nerolidol 2 in the W1 extract was 22.78%; in the N1 extract, it was 34.94%; in the G1 extract it was 74.81% and in the M1 extract it was 15.05% Furthermore, a value of 0% only indicates a concentration of analyte below the limit of detection and not necessarily the absence of the analyte.

As can be seen, the essential oil fraction contains several compounds which are known or suspected of having antimicrobial properties, for example, but by no means limited to: a-pinene, B-ionone, b-pinen, caryophyllene, caryophyllene oxide, citral, citronellol, farnesene, geraniol, geranyl acetate 1, geranyl acetate 2, humulene, limonene, and linalool.

As can be seen in both Tables 21 and 22, the percentage content of the various compounds varies somewhat between the different varieties tested. As discussed herein, this likely accounts for at least some of the differences in efficacy between the different extracts.

An aqueous hop extract for use as an anti-microbial comprising an effective amount of one or more, two or more, three or more or four or more of the group consisting of: humulene, caryophyllene, myrcene, farnesene, linalool, nerodiol and limolene and/or an effective amount of one or more, two or more, or three of the group consisting of: iso-cohumulone, iso-humulone and iso-adhumulone.

In some embodiments of the invention, the aqueous hop extract comprises an effective amount of at least one or at least two of or of humulene, caryophyllene and myrcene, wherein the "effective amount" has an antimicrobial effect on at least one microorganism, for example, at least one of: *Clostridium difficile; Ophiostoma ulmi; Clostridium botulinum; Stachybotrys chartarum; Bacillus atrophaeus; Trichophyton rubrum; Bacillus anthracis Sterne; Bacillus cereus; Clostridium sporogenes; Pseudomonas aeruginosa, Salmonella enterica* (formerly *Salmonella choleraesuis*), *Klebsiella pneumoniae, Enterobacter aerogenes* (alternately known as *Klebsiella aerogenes*), and *Escherichia coli; Fusarium oxysporum, F. culmorum, F. semitectum, Candida albicans, Candida krusei, Candida tropicalis, Candida parasilosis, Trichophyton interdigitale* (formerly *Trichophyton mentagrophytes*), *Aspergillus fumigatus, Fusarium graminearum; Cryptococcus gattii; Mycobacterium bovis* (BCG); *Mycobacterium terrae; Botrytis cinerea, Agrobacterium vitis, Elsinoe ampelina, Penicillium* spp., *Gluconobacter cerinus, Gluconobacter albidus, Gluconobacter frateurii, Pichia kluyveri, Plasmopara viticola, Uncinula necator, Guignardia bidwelli, Rhizopus* spp, *Candida* spp., and *Hanseniaspora uvarum;*

According to another aspect of the invention, there is provided an anti-microbial aqueous hop extract as described above.

In some embodiments of the invention, the anti-microbial product or anti-microbial aqueous hop extract is a boiled water hop extract, as described herein.

Furthermore, metabolomic analysis of the hop genome indicated that these varieties are also capable of producing a number of antimicrobial compounds, for example, including but by no means limited to 2-undecanone, dibenzofuran, furfural, hydroxy-benzoic acids, polyhydroxy-benzoic acids, olivetol, olivetolic acid, patulin, protocatechuic acid, protocatechuic aldehyde, salicylic acid, salicylaldehyde, resveratrol, umbellaferone, xanthohumol and trans-caffeic acid.

Accordingly, in other embodiments of the invention, the aqueous hop extract or the boiling water hop extract may be prepared from or may be a combination of two or more different varieties of hop so as to produce an anti-bacterial product with the desired anti-bacterial profile, as discussed herein.

It is noted that, as discussed therein, while the antibacterial properties of hop varieties against Gram-positive bacteria are known, hop plant extracts were at the time considered to not have significant anti-bacterial activity against Gram Negative bacteria. However, given that different hop varieties encounter a wide variety of different microbial pathogens, it is expected that hop plant extracts, particularly the hop cone boiling water extract described herein, will have anti-bacterial properties against other microbial pathogens, for example other bacteria that are not common soil pathogens, Gram-negative bacteria, fungi and other microbes, as discussed herein.

Furthermore, as discussed herein, the hop extracts have been demonstrated to eradicate biofilm produced by the Gram-positive bacteria tested. As such, it is maintained that it is a strong prediction that, given the differences in the nature of these biofilms, that the boiling water hop extract will eradicate biofilm created by all Gram-positive bacteria capable of creating a biofilm.

Examples of other bacteria that are not common soil pathogens include but are by no means limited to *Clostridium difficile; Ophiostoma ulmi; Clostridium botulinum; Stachybotrys chartarum; Bacillus atrophaeus; Trichophyton rubrum; Bacillus anthracis Sterne; Bacillus cereus*; and *Clostridium sporogenes*.

Examples of Gram-negative bacteria include but are by no means limited to *Pseudomonas aeruginosa, Salmonella enterica* (formerly *Salmonella choleraesuis*), *Klebsiella pneumoniae, Enterobacter aerogenes* (alternately known as *Klebsiella aerogenes*), and *Escherichia coli* (including but by no means limited to O26:H11, O157:H7, O103, O121, O126, O26 and O157).

Examples of fungi include but are by no means limited to *Fusarium oxysporum, F. culmorum, F. semitectum, Candida albicans, Candida krusei, Candida tropicalis, Candida parasilosis, Trichophyton interdigitale* (formerly *Trichophyton mentagrophytes*), *Aspergillus fumigatus, Fusarium graminearum* and *Cryptococcus gattii*.

Examples of other microbes include but are by no means limited to *Mycobacterium bovis* (BCG) and *Mycobacterium terrae*.

Examples of wine grape pathogens include but are by no means limited to *Botrytis cinerea, Agrobacterium vitis, Elsinoe ampelina, Penicillium* spp., *Gluconobacter cerinus, Gluconobacter albidus, Gluconobacter frateurii, Pichia kluyveri, Plasmopara viticola, Uncinula necator, Guignardia bidwelli, Rhizopus* spp, *Candida* spp., and *Hanseniaspora uvarum*.

As discussed herein, the compound or compounds responsible for the anti-microbial activities of the aqueous hop extract and the boiling water hop extract are water soluble. Some of these compounds appear to be secreted, and may be secreted by the hop plant as part of the plant's natural anti-microbial defences. As will be apparent to those of skill in the art, it is not unexpected that plants would secrete antibacterial compounds and as discussed above it is known in the art.

However, it is unexpected that a boiling water hop extract would have greater anti-bacterial activity than one prepared at a lower temperature. Specifically, one of skill in the art would expect that boiling water would denature any antibacterial peptides or proteins and may also degrade or otherwise alter any chemical compounds. In addition, the bet-acids are known to be highly unstable. Furthermore, heating would also likely remove the monoterpenes, many of which are known to have antimicrobial properties. As such, one of skill in the art would in fact predict that a boiling water extract of hop plants, for example, hop cones, leaves and/or stems, would in fact have reduced antibacterial activity compared to a lower temperature aqueous extract.

While not wishing to be bound to a particular theory or hypothesis, it is noted this suggests that it is unlikely that the anti-bacterial activities are protein-based and accordingly are likely to be compounds synthesized and secreted by the plant.

However, it is unclear how such an antibacterial activity would increase on boiling, unless one or more of these antibacterial compounds were membrane-bound and/or otherwise assumes a different conformation and/or structure subsequent to heating.

Alternatively, it is possible that at least one of the antibacterial compounds released by the hop cones on exposure to boiling water is a peptide or protein that is membrane-bound that is denatured on boiling but that resumes its proper orientation on exposure to a bacterial membrane.

As will be appreciated by one of skill in the art, the individual components of the boiling water hop extracts from the different varieties can be isolated and identified by any suitable means known in the art, for example, by any of the various fractionation and/or purification methods known in the art. Identification of the strain-specific activities of these different compounds can be facilitated by comparison of their relative concentrations in the extracts prepared from the different hop varieties, based on the knowledge of the effectiveness of the different extracts on specific Gram-positive bacteria.

Of particular interest is the potent antimicrobial activity of agents obtained from the boiling water hop extract against the human pathogen *S. aureus*. As described above, the treatment of *S. aureus* infections using commercially approved antibiotics is increasingly difficult due to the rise in antibiotic strains of this organism. The antimicrobial compounds from the boiling water hop extracts, however, completely inhibited the growth of the *S. aureus* bacterium. Accordingly, in one embodiment of the invention, these antimicrobial agents are candidate therapeutics for treating *S. aureus* infections.

While the exact mechanism by which the antimicrobial compounds from hop exert bacterial growth inhibition activity is unknown, it is clear from the data in the accompanying tables, discussed above that the boiling water hop extracts are effective at arresting the growth of evolutionary distant Gram-positive bacteria. For example, the inventive antimicrobial compounds are equally effective at arresting the growth of *B. subtilis* and *Staphylococcus aureus*, which are both Gram Positive bacteria. However, from an evolutionary perspective, *B. subtilis* and *S. aureus* are not closely related. Thus, the present inventors hypothesize that the antimicrobial activity of the aqueous hop extract, the boiling water hop extract and/or antibacterial compounds isolated therefrom is broad and capable of inhibiting or arresting bacterial cell growth of many different strains of bacteria, especially Gram-positive strains of bacteria.

However, it is possible that other hop plant parts, for example, the stalks of the plants, may secrete higher levels of the compound(s) responsible for the anti-microbial activity or may secrete additional anti-microbial compounds. Furthermore, different extraction conditions, for example, longer incubation and/or greater agitation during incubation and/or different solvents, may result in more concentrated or higher concentrations of anti-microbial activity.

It is of note that the variability in effectiveness of the hop extract against different microorganisms based on the hop variety used indicates that the hop extracts would be less likely to undergo resistance given that the analytical and metabolomic analyses suggest the presence of a number of compound classes each with member compounds known or suspected to have antimicrobial activity, thereby circumventing the ability of the various pathogens to develop resistance in the normal fashion of having to deal with a single antimicrobial agent.

As will be appreciated by one of skill in the art, the plant-derived material comprising the anti-microbial activity may be used in the preparation of a number of anti-microbial products, for example, pharmaceuticals, disinfectants, anti-microbial creams, skin treatment creams and the like. As will be appreciated by one of skill in the art, such products could be identified as being "natural" or "all-natural" anti-microbial products.

For example, a "natural" or "all-natural" surface disinfectant could be prepared with the aqueous hop extract or boiling water hop extract prepared as described herein as the active ingredient. As will be appreciated by one of skill in the art, such a surface disinfectant could be used to treat surfaces at risk of contamination by for example *S. aureus, E. faecium, L. monocytogenes, S. pneumonia* as well as other similarly infectious Gram-positive bacteria. It is of note that in some embodiments, such a disinfectant might have a mixture of extracts from suitable hop varieties, that is, hop varieties known to be highly effective against targeted bacterial strains, as the active ingredient. In other embodiments, the active ingredient for the disinfectant product may be one or more compounds isolated or purified from an aqueous hop extract or boiling water extract prepared as described herein identified as having particular activity against a bacterial strain of interest. It is of note that such a disinfectant could be used for treatment of surfaces such as floors, countertops, curtains and the like in for example hospitals and care homes where individuals who are particularly at risk of infections by bacteria such as these and who may also benefit from, that is, not react adversely to, a natural disinfectant product.

In other embodiments, a skin treatment product for treatment and/or prevention of infection by bacterial strains such as for example, *C. acnes, S. aureus*, MRSA, *B. subtilis*, VRE and *L. monocytogenes*, as discussed herein.

Furthermore, as discussed above, bacteria-specific compounds, as discussed above, can be isolated and used in bacteria-specific products, as discussed herein.

As discussed herein, the extract can be used as an antibacterial agent, for example, a pharmaceutical or a disinfectant against bacteria and/or biofilms formed by bacteria. Accordingly, in some embodiments, the extract may be combined with another compound or composition having antibiotic properties. In other embodiments, as discussed herein, the extract can be formulated specifically for use against Gram-positive pathogens and/or may be formulated for topical or oral administration.

Described herein is the preparation of an aqueous hop extract and a boiling water hop extract prepared from dried hop cones that were ground prior to extraction and use thereof against *P. larvae*, as discussed herein and then extracted with either water or boiling water, as discussed herein. While the terms "water hop extract", "hop water extract", "aqueous hop extract" and "hop aqueous extract" for example may be used herein interchangeably in some cases, these terms all refer to an extract prepared by water extraction of a ground quantity of hops, for example, hop cones.

Specifically, the hop extracts are active against the Gram-positive honeybee pathogen *Paenibacillus larvae*, particularly the biofilm and spores, as discussed below.

Furthermore, the boiling water extract is also effective against *Varroa*, as shown in Table 23. As such, as discussed herein, the boiling water hops extract can be applied to bees, for example, by mixing the boiling water extract with the water supply. As known to those of skill in the art, the bees in the hive not only drink from the water supply, worker bees cool the hive by fanning water droplets throughout the hive, meaning that the bees in the hive are essentially bathed in water from the water supply, thereby providing an "all in one" bee treatment that affects both the mites and the bacteria as well as the spores of the bacteria, as discussed herein. Furthermore, in addition to reducing the counts or levels of the mites, spores and bacteria, the hops water extract or hops boiling water extract will also reduce biofilm formation by *P. larvae*, as well as reduce the level of spore contamination. In other embodiments, the boiling water hops extract can be mixed with the bee sugar, thereby protecting the bees against the spores post-ingestion as well.

While a mixture of potassium salts of beta acids including lupulone, colupulone and adlupulone has been used to treat *Varroa* mite infestations, the mixture was delivered from cardboard strips including added antioxidants and thixotropic material such fumed silica. (Published US Patent Application 2019/0343126)

As discussed below, the anti-biofilm activity was expressed as the Minimum Biofilm Eradication Concentration (MBEC), defined as the lowest concentration of test article yielding a log10 reduction in colony forming units (CFU) of >3 (corresponding to >99.9% reduction). A semi-quantitative assessment (i.e., turbidity assay) of bacteriostatic (MIC) and bactericidal (MBC) effects against planktonic bacteria, as well as anti-biofilm activity (MBEC), was also performed.

As discussed herein, the *P. larvae* tested in this work were cultured such that they were likely almost entirely in the vegetative state.

For all four tested hop extracts, MBCs, MICs, and MBECs were below the minimum observable levels (i.e., less than the minimum concentration tested), indicating that *P. larvae* biofilms are extremely sensitive to all four hop extracts, as discussed below.

Furthermore, the boiling water extract has antimicrobial efficacy against a spore-enriched *P. larvae* preparation, as discussed below.

According to an aspect of the invention, there is provided a method of preparing an anti-*P. larvae* composition and/or an anti-*Varroa* mite composition comprising grinding a quantity of hop cones from the hop plant suspending the ground hop cones in water, boiling the suspension for at least about 15, 20 or 30 minutes and recovering the supernatant.

According to an aspect of the invention, there is provided a method for treating, preventing or reducing the severity of American Foulbrood and/or *Varroa* mite infestation comprising: grinding a quantity of hop cones from hop plants, suspending the ground hop cones in water, boiling the suspension for at least about 15, 20 or 30 minutes, recovering the supernatant, thereby providing a hop water extract or a boiled water hop extract, applying the hop water extract or the boiled water hop extract to a honeybee hive.

As discussed above and as demonstrated in Table 24, it is important to note that the boiling water hops extract is also effective against European foulbrood, despite the fact that this disease is caused by a different bacterium (*M. plutonius*) which does not produce spores or a biofilm and that produces different symptoms and has different control requirements than AFB. However, similar application methods may be used for treatment and/or prevention of EFB in bee hives as for treatment and/or prevention of AFB.

In some embodiments of the invention, the hop water extract or boiled water hop extract is formulated as a spray to be applied within the honeybee hive.

In some embodiments of the invention, the hop water extract or the boiled water hop extract is formulated as a disinfecting wash. In some embodiments, the disinfecting wash may be applied to a suitable carrier so that the wash can be administered as part of a disinfecting wipe. Herein, the terms "disinfecting wash" and "disinfecting wipe" are used interchangeably and indicate either the disinfecting wash in solution or in combination with a suitable application system or device.

In some embodiments of the invention, the spray or disinfecting wash is applied to the honeybee hive 24 hours prior to the setting of honeybee larvae in the brood combs in the honeybee hive.

In some embodiments of the invention, the spray or disinfecting wash is applied to the honeybee hive by application on tools and equipment used for maintenance in the honeybee hive.

In some embodiments of the invention, the spray or the disinfecting wash is applied to honeybees for controlling *Paenibacillus larvae* bacteria, for example, *P. larvae* growth on the honeybees and/or *P. larvae* spores and/or for controlling *Varroa* mites.

In some embodiments of the invention, the hop water extract or the boiled water extract is applied to the honeybee hive by adding the hop water extract or the boiled water extract to the honeybee hive water supply, that is, by mixing the hop water extract or the hop boiled water extract with the water source for the honeybee hive. As known to those of skill in the art, all bee hives are supplied with a water source. The bees drink it because they are thirsty and they also use water to help cool off the hive by spreading thin films of water throughout the hive. As such, mixing the extract into the water supply would prevent the bacteria from infecting the bees or at least prevent vegetative growth of the bacteria when the bees drink. At the same time, the treated water would be spread throughout the hive by the bees, coming in contact with both the mites, the bacterium and, most importantly, with the endospores, as discussed herein. As discussed above, in some embodiments of the invention, the hops water extract or the hops boiled water extract may be applied to the bees by mixing the extract with the bee sugar syrup. In these embodiments, the hops water extract and/or the hops boiled water extract may be formulated for mixing with the bee sugar syrup.

In some embodiments of the invention, the hop water extract or the boiled water hop extract treats, prevents and/or reduces the severity of American Foulbrood by reducing biofilm formation by *Paenibacillus larvae* bacteria or by inhibiting vegetative growth of *P. larvae* and/or by reducing *P. larvae* spore counts. In some embodiments of the invention, the bacteria are resistant to broad-spectrum antibiotics, such as sulfathiazole and oxytetracycline hydrochloride (OTC).

As discussed above, the boiling water hop extracts also trat, prevent and/or reduce the severity of European Foulbrood by inhibiting vegetative growth of *M. plutonius.*

As discussed herein, the compound or compounds responsible for the anti-*M. plutonius* and anti-*P. larvae* activities of the aqueous hop extract and the boiling water hop extract are water soluble. Some of these compounds appear to be secreted, and may be secreted by the hop plant as part of the plant's natural anti-microbial defences. As will be apparent to those of skill in the art, it is not unexpected that plants would secrete antibacterial compounds and as discussed above it is known in the art. However, it is surprising that Hops would secrete compounds that are effective against *M. plutonius, P. larvae* and *Varroa*, which are not Hops pathogens.

Furthermore, it is unexpected that a boiling water hop extract would have greater anti-*M. plutonius* and anti-*P. larvae* activity than one prepared at a lower temperature. Specifically, one of skill in the art would expect that boiling water would denature any antibacterial peptides or proteins and may also degrade or otherwise alter any chemical compounds. In addition, the bet-acids are known to be highly unstable. Furthermore, heating would also likely remove the monoterpenes, many of which are known to have antimicrobial properties. As such, one of skill in the art would in fact predict that a boiling water extract of hop plants, for example, hop cones, leaves and/or stems, would in fact have reduced antibacterial activity compared to a lower temperature aqueous extract.

While not wishing to be bound to a particular theory or hypothesis, it is noted this suggests that it is unlikely that the anti-*M. plutonius* and anti-*P. larvae* activities are protein-based and accordingly are likely to be compounds synthesized and secreted by the plant.

However, it is unclear how such an antibacterial activity would increase on boiling, unless one or more of these antibacterial compounds were membrane-bound and/or otherwise assumes a different conformation and/or structure subsequent to heating.

Alternatively, it is possible that at least one of the antibacterial compounds released by the hop cones on exposure to boiling water is a peptide or protein that is membrane-bound that is denatured on boiling but that resumes its proper orientation on exposure to a bacterial membrane.

As will be appreciated by one of skill in the art, the individual components of the boiling water hop extracts from the different varieties can be isolated and identified by any suitable means known in the art, for example, by any of the various fractionation and/or purification methods known in the art. Identification of the strain-specific activities of these different compounds can be facilitated by comparison of their relative concentrations in the extracts prepared from the different hop varieties, based on the knowledge of the effectiveness of the different extracts on specific Gram-positive bacteria.

However, it is possible that other hop plant parts, for example, the stalks of the plants, may secrete higher levels of the compound(s) responsible for the anti-microbial activity or may secrete additional anti-microbial compounds. Furthermore, different extraction conditions, for example, longer incubation and/or greater agitation during incubation and/or different solvents, may result in more concentrated or higher concentrations of anti-microbial activity.

For example, a "natural" or "all-natural" surface disinfectant could be prepared with the aqueous hop extract or boiling water hop extract prepared as described herein as the active ingredient.

For example, given the anti-biofilm properties of the boiling water hop extract described herein, the extract or compounds isolated therefrom may be combined with a suitable antibiotic as described above. As such, this antibacterial composition will have improved anti-bacterial properties in that in addition to anti-bacterial properties on its own, the boiling water extract of hops will also either breakdown or interfere with the formation of or reduce the formation and/or density of bacterial biofilms, as discussed herein.

Pharmaceutical Compositions and Uses Thereof

The hop aqueous extract, hop boiling water extract and/or compounds isolated therefrom obtained using the process described above may be formulated at a dose that is therapeutically effective to stop or reduce bacterial infection. In one embodiment, the hop aqueous extract, hop boiling water extract and/or compounds isolated therefrom are formulated as a topical medication, such as a foam, a cream, a lotion or a gel. The hop aqueous extract, hop boiling water extract and/or compounds isolated therefrom are potent inhibitors of S. aureus cell growth. As described above, S. aureus infection poses a significant health challenge to patients in hospitals. Illness can range from minor skin infections, such as pimples and abscesses, to life-threatening diseases such as pneumonia, meningitis, osteomyelitis, endocarditis, toxic shock syndrome, bacteremia, and sepsis. Such life-threatening infections are treated by systemic administration of a therapeutically effective formulation of the aqueous hop extract, the boiling water hop extract and/or compounds isolated therefrom.

The hop aqueous extract, hop boiling water extract and/or compounds isolated therefrom possessing antimicrobial activity are administered to a patient or subject in need of treatment for localized or systemic bacterial infections. These compounds are administered alone or in combination with other compounds having similar or different biological activities. For example, the aqueous hop extract, the boiling water hop extract and/or antibacterial compounds isolated therefrom can be administered in combination therapy, either simultaneously or within minutes, hours, or days of another therapeutic agent.

The therapeutically effective dose of the hop aqueous extract, hop boiling water extract and/or compounds isolated therefrom may be formulated as a single dose or may be formulated as a multi-dose formulation that can be administered over several days. Examples of combination therapies include administering a composition comprising an aqueous hop extract, a boiling water hop extract and/or antibacterial compounds isolated therefrom with other pharmaceutical agents used to treat bacterial infections, for example, antibiotics.

Antibacterial antibiotics are commonly classified based on their mechanism of action, chemical structure, or spectrum of activity. Most antibacterial antibiotics target bacterial functions or growth processes. Penicillins and cephalosporins target the bacterial cell wall by interfering with cell wall synthesis, while polymyxins target the bacterial cell membrane. Some antibacterial antibiotics interfere with the synthesis or function of essential bacterial enzymes, for example, rifamycins, lipiarmyeins, quinolones and sulfonamides. Such antibacterial antibiotics have bactericidal activity, while antibacterial antibiotics such as macrolides, lincosamides and tetracyclines target protein synthesis and are usually bacteriostatic in nature.

Illustrative of the class "antibiotics" are compounds that reduce or inhibit bacterial cell growth. Exemplary antibiotic compounds that can be used in combination with the hop aqueous extract, hop boiling water extract and/or compounds isolated therefrom of the invention include but are by no means limited to penicillin, erythromycin, clindamycin, gentamycin, tetracycline, meclocycline, ceftolozane, tazobactam, ceftazidime, avibactam, ceftaroline, imipenem, plazomicin, eravacycline, bacitracin, brilacidin, azithromycin, amoxicillin, augmentin, ticarcillin, ampicillin, piperacillin, tazobactam, cefoperazone, tazocin, avibactam, avycaz, sublactam, and the drug efflux inhibitory peptide Phe-Arg-β-naphthylamide.

For example, given the anti-biofilm properties of the boiling water hop extract described herein, the extract or compounds isolated therefrom may be combined with a suitable antibiotic as described above. As such, this antibacterial composition will have improved anti-bacterial properties in that in addition to anti-bacterial properties on its own, the boiling water extract of hops will also either breakdown or interfere with the formation of or reduce the formation and/or density of bacterial biofilms, as discussed herein.

The hop aqueous extract, hop boiling water extract and/or compounds isolated therefrom can be administered or can be formulated to be administered orally, topically, parenterally, by inhalation or spray or rectally in dosage unit formulations. The term "parenteral" as used herein includes subcutaneous injections, intravenous, intramuscular, intrasternal injection or infusion techniques.

Suitable oral compositions in accordance with the invention include without limitation tablets, troches, lozenges, aqueous or oily suspensions, dispersible powders or granules, emulsion, hard or soft capsules, syrups or elixirs. Of course, as discussed herein, it is important to note that the boiling water extract of the invention is prepared by boiling of the hop plant parts, for example, the hop cones, for much longer, for example, at least about 15, 20 or 30 minutes, compared to preparations such as herbal teas made from hop plant parts and are accordingly distinguished therefrom on that basis.

Encompassed within the scope of the invention are pharmaceutical compositions suitable for single unit dosages that comprise the hop aqueous extract, hop boiling water extract and/or compounds isolated therefrom and a pharmaceutically acceptable carrier.

In one embodiment, the invention provides an oral or injectable formulation of the hop aqueous extract, hop boiling water extract and/or compounds isolated therefrom. Oral formulations of the hop aqueous extract, hop boiling water extract and/or compounds isolated therefrom can be in the form of a liquid, a tablet or a gelatin capsule. Such formulations may contain one or more agents selected from the group consisting of sweetening agents, flavoring agents, coloring agents and preserving agents in order to provide pharmaceutically elegant and palatable preparations of such compounds.

Injections are manufactured by dissolving a therapeutically effective dose of the aqueous hop extract, boiling water hop extract and/or antibacterial compounds isolated therefrom in a suitable carrier. The solution of the hop aqueous extract, hop boiling water extract and/or compounds isolated therefrom in carrier is sterilized by passing the solution through a sterile filter. Protocols for making sterile injections are well known in the formulary art. Among the acceptable vehicles and solvents that may be employed as carriers are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables. Adjuvants such as local anesthetics, preservatives and buffering agents can also be added to parenteral compositions.

Inventive compositions suitable for oral use may be prepared according to any method known to the art for the manufacture of pharmaceutical compositions. For instance, liquid formulations of the hop aqueous extract, hop boiling water extract and/or compounds isolated therefrom can contain one or more agents selected from the group consisting of sweetening agents, flavoring agents, coloring agents and preserving agents in order to provide pharmaceutically elegant and palatable preparations of the hop extracts, as discussed herein.

For tablet compositions, the active ingredient in admixture with non-toxic pharmaceutically acceptable excipients is used for the manufacture of tablets, for example, by lyophilizing the extract and then using the resulting powder in a tableting process known in the art, or to fill gelatin capsules. Other suitable methods will be readily apparent to one of skill in the art. Exemplary of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, the hop aqueous extract, hop boiling water extract and/or compounds isolated therefrom is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally occurring phosphatide, for example, lecithin, polyoxyethylene stearate, heptadecaethyleneoxycetanol, polyoxyethylene sorbitol monooleate, polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the hop aqueous extract, hop boiling water extract and/or compounds isolated therefrom in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, or an aqueous suspension. This suspension may be formulated according to the known art using those suitable dispersing or wetting agents and suspending agents. The sterile injectable preparation may also be sterile injectable solution or suspension in a non-toxic parentally acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

The total amount by weight of the hop aqueous extract, hop boiling water extract and/or compounds isolated therefrom in a pharmaceutical composition is from about 0.1% to about 95%. By way of illustration, the amount of the hop aqueous extract, hop boiling water extract and/or compounds isolated therefrom by weight of the pharmaceutical composition can be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

In one embodiment, the pharmaceutical composition comprises a total amount by weight of the hop aqueous extract, hop boiling water extract and/or compounds isolated therefrom of about 1% to about 10%; about 2% to about 10%; about 3% to about 10%; about 4% to about 10%; about 5% to about 10%; about 6% to about 10%; about 7% to about 10%; about 8% to about 10%; about 9% to about 10%; about 1% to about 9%; about 2% to about 9%; about 3% to about 9%; about 4% to about 9%; about 5% to about 9%; about 6% to about 9%; about 7% to about 9%; about 8% to about 9%; about 1% to about 8%; about 2% to about 8%; about 3% to about 8%; about 4% to about 8%; about 5% to about 8%; about 6% to about 8%; about 7% to about 8%; about 1% to about 7%; about 2% to about 7%; about 3% to about 7%; about 4% to about 7%; about 5% to about 7%; about 6% to about 7%; about 1% to about 6%; about 2% to about 6%; about 3% to about 6%; about 4% to about 6%;

about 5% to about 6%; about 1% to about 5%; about 2% to about 5%; about 3% to about 5%; about 4% to about 5%; about 1% to about 4%; about 2% to about 4%; about 3% to about 4%; about 1% to about 3%; about 2% to about 3%; or about 1% to about 2%.

As used herein, the terms "about" and "approximately" refer to the base value plus or minus 5%. That is, reference to "about 100" refers to any value between 95-105 inclusive.

As discussed below, *P. aeruginosa* was not susceptible to any of the tested extracts (i.e., no inhibition in challenge, outgrowth, or MBEC recovery plates and no log10 reductions).

*S. enterica* was not inhibited in the challenge, outgrowth, or recovery plates (i.e., MIC, MBC, and MBEC all >100%), but a significant log10 reduction of 0.62 was observed for the W1 extract and a larger but statistically insignificant log10 reduction of 1.3 was observed for M1.

*E. coli* was not inhibited in the challenge, outgrowth, or recovery plates (i.e., MIC, MBC, and MBEC all >100%), but significant log10 reductions of 2.4 and 2.3 were observed for the M1 and N3 extracts, while reductions of 1.0 and 3.4 for W1 and G2, respectively, did not reach the significance threshold of P<0.05.

*A. vitis* was not inhibited in the challenge and outgrowth plates (i.e., MIC and MBC >100%). Pilot work was conducted to optimize growth and handling conditions for *A. vitis*: The optimal temperature was confirmed to be 26° C.; agar cultures required 48 hours for distinct, countable colonies to form; broth cultures reached saturation (density of ~$10^6$ CFU/mL) in 24 hours; biofilms required 48 hours to form on polystyrene pegs (with low densities recovered, indicating formation of poor biofilms on this surface). Despite this, no growth was observed in the biofilm recovery plate (meaning that no MBEC could be calculated), and no colonies were counted, thus yielding no quantitative log reduction.

*S. aureus* yielded MIC values of 6.25, 3.13, 3.13, and ≤1.56% for M1, W1, N3, and G2 extracts, respectively, with proportionately higher MBC values (25, 12.5, 12.5, and 6.25%) and higher MBEC values (50, 25, 50, and 12.5%). Relative to the saline control, the undiluted extracts all yielded log10 biofilm reductions of 3.65 (representing a complete loss of viability).

MRSA results were similar to those for *S. aureus*. Note: Few colonies were obtained for the saline control wells immediately after sonication of the MBEC lid, complicating the calculation of Log10 reductions. Thus, serial dilution/spot plating was repeated for the same wells of this recovery plate after the 24-hour incubation period, yielding the log reduction shown below for this organism.

*L. monocytogenes* yielded MIC values of 3.13, 3.13, 3.13, and ≤1.56% for M1, W1, N3, and G2 extracts, respectively, with proportionately higher MBC values (25, 25, 25, and 12.5%) and higher MBEC values (100% for all four extracts). Relative to the saline control, the undiluted extracts all yielded log10 biofilm reductions of 3.31 (representing a complete loss of viability).

*E. faecium* yielded MIC values of 6.25, 6.25, 6.25, and 3.13% for M1, W1, N3, and G2 extracts, respectively, with proportionately higher MBC values (100, 100, 100, and 50%) and higher MBEC values (100% for all four extracts). Relative to the saline control, the undiluted extracts all yielded log10 biofilm reductions of 2.72 (representing a complete loss of viability).

*C. albicans* was either not susceptible to the hop extracts (based on MIC, MBC, and MBEC values), or was killed simply by distilled water (based on the log reductions).

Note: Few colonies were obtained for the saline control wells immediately after sonication of the MBEC lid, complicating the calculation of Log10 reductions. Thus, serial dilution/spot plating was repeated for the same wells of this recovery plate after the 24-hour incubation period, yielding the log reduction shown below.

As expected, MBCs tended to be higher than MICs, with MBECs being higher still. This suggests that the hop extracts tested here are, like other antimicrobial agents, more potent as bacteriostatic agents than as bactericidal agents, and that biofilms are generally less susceptible to antimicrobials than planktonic cells.

The main exception was *P. aeruginosa*, which was not susceptible to any of the tested extracts, possibly reflecting the general robustness of its biofilms. *A. vitis* and *C. albicans* were also not inhibited by the hop extracts tested.

The invention will now be further explained and/or elucidated by way of example; however, the invention is not necessarily limited to and/or by the examples.

EXAMPLES

Example 1—Extract Preparation

In one embodiment, the plant material may be pre-treated prior to extraction of the hop plant material, for example, the hop cones. For example, the plant material is cut or ground to a small particulate substance prior to preparation of the extract. Alternatively, enzymatic treatment, freezing and thawing of the plant material or swelling of the plant material by soaking in water, alcohol or a water-alcohol mixture may be performed prior to extraction.

In some embodiments of the invention, the particle size of the plant material is reduced for example by mortar and pestle grinding, by auto-grinding, or other similar methods known in the art for reducing the size of the particles. In some embodiments, extraction efficiency increases with particle size reduction of the ground hop material. Depending on the chemical nature of the compounds to be extracted, the plant material may be steamed or cooked prior to extraction. Pre-treatment by subjecting the plant material to high pressure can be used to increase porosity and improve extraction efficiency. Maceration, which is a process of extracting chemical compounds from pulverized plant material using a cold solvent may be used if the compound of interest is thermally unstable. Alternatively, a solvent is percolated through plant material or through coarsely ground up plant material to extract the compound of interest.

The hop aqueous extract, hop boiling water extract and/or compounds isolated therefrom can be distilled to obtain concentrated residue. In one embodiment, the solvent is distilled and reused for extraction. The crude mixture of hop compounds may be purified prior to pharmaceutical use. Purification is performed by use of various chromatographic techniques, including adsorption chromatography, partition chromatography, ion-exchange chromatography, gel chromatography, or affinity chromatography. As will be appreciated by one of skill in the art, "purification" does not require absolute purity, but only requires that the concentration of the desired compounds is increased and/or that undesired compounds are removed.

In some embodiments, the aqueous hop extract is lyophilized and then reconstituted in water prior to use.

Preparation of Extracts

The following are examples of hop extractions.

30 minutes of heating slurry extracts because they seem to be strongest in antimicrobial activity. Hops samples: heated for at least about 15 minutes, at least about 20 minutes or preferably at least about 30 minutes, rolling boil (~100° C.). Surprisingly, boiling for longer than 30 minutes has virtually no effect on efficacy of the extract.

Magnum: weighed out: 1.35 g; grounded: 1.21 g (oiliest consistency, saw the most lupulin glands); black mortar and pestle after using it with Centennial; placed in 50 mL flask with aluminum foil lid; Added 24.2 mL of Water.

Crystal: weighed out: 1.29 g, grounded 1.21 g (Driest consistency), used white mortar and pestle, placed in 125 mL flask with 25 mL flask on top; Added 24.2 mL of Water.

Centennial: weighted out 1.29 g; ground: 1.20 g; used black mortar and pestle; placed in 125 mL flask with 25 mL flask on top; Added 24 mL of Water Stored in 4° C. to cool down.

Example 2—MIC Values

Hop is weighed out and added to water at a ratio of 0.02-2.0 g to 20 ml of water.

Extract allowed to boil for 30 minutes.

After boiling, extract is allowed to cool to reasonable temperature (<45° C.). Extract may be centrifuged to pellet plant material and the liquid is collected or ground hop extract is filtered, for example, passed through a grade 1 Whatman filter paper to filter out plant material. Liquid extract is than portioned into smaller aliquots and frozen at −80° C. until it is used.

Minimum inhibitory concentration (MIC) testing is carried out in compliance with CLSI standards. In brief, organism is cultures to a high optical density (OD). It is then diluted to an OD that matches a 0.5 McFarland turbidity standard (equivalent to an optical density of a bacterial suspension $1.5\times10^8$ colony forming units (CFU/ml)). The culture is then further diluted by a factor 10,000 leading to a final CFU of $1.5\times10^4$.

The suspension is then seeded into media containing a gradient of hop concentrations at a final CFU of $3\times10^8$. The culture is than allowed to grow at 37° C. for 18 hours. The optical density is than measured by eye (no visible growth is considered the MIC). In addition, Resazurin is added to the MIC plate to measure respiration rate. Generally, optical density and respiration match. In the case of the gram-negative bacteria optical density suggests no effect by the hop extract; however, respiration is affected at the high concentrations of hop extract.

Results

MIC concentrations of hop extracts are listed in Table 1. All numbers are shown as percent (%). Lower numbers indicate stronger inhibition of growth.

Example 3—Dis Diffusion Testing

In brief, organism is cultures to a high optical density (OD). It is then diluted to an OD that matches a 0.5 McFarland turbidity standard (equivalent to an optical density of a bacterial suspension $1.5\times10^8$ colony forming units (CFU/ml). A sterile cotton swab is then allowed to soak in suspension and then is swabbed across an agar plate to provide an even lawn of culture. Disks which have been loaded with 20 μl of hop extract are then places on the plates. The culture is than allowed to grow at 37° C. for 18 hours. The size of the zone of clearance around each disk is than measured in mm.

Results

Zones of inhibition of hop extracts are shown in Table 2. All numbers are shown as millimetres (mm). Larger numbers indicate stronger inhibition of growth.

In terms of zones of inhibition Galena produced the largest inhibition closely followed by Willamette, while Saaz and Crystal were the least effective, based on total sum of activity.

MIC results suggest that Willamette followed by Galena had the strongest effect while Saaz and Crystal were the weakest, based on total sum of activity.

As a general trend, when looking at MIC data, Willamette and Galena appear in the top 3 for every bacterial strain that is affected, with Cashmere being the second most frequent, corroborating the general sum results. When examining disk diffusion results by strain, the top scoring hop varieties are Galena and Hallertau with Willamette, Cascade, Cashmere all in second.

Example 4—Biofilm

This work comprises a screen of hop extracts for antimicrobial efficacy against a panel of organisms. The main focus was anti-biofilm efficacy, measured as the Minimum Biofilm Eradication Concentration (MBEC); however, bacteriostatic and bactericidal efficacy against planktonic cells was also measured, yielding the MIC (Minimum Inhibitory Concentration) and MBC (Minimum Bactericidal Concentration), respectively. Finally, in order to complement the semi-quantitative determination of MIC, MBC, and MBEC (which rely on an assessment of growth versus total inhibition), the log10 reduction in colony forming units (CFU) was quantified for the undiluted hop extracts, relative to the saline growth control.

As expected, MBCs tended to be higher than MICs, with MBECs being higher still. This suggests that the hop extracts tested here are like other antimicrobial agents: more potent as bacteriostatic agents than as bactericidal agents, and that biofilms are generally less susceptible to antimicrobials than planktonic cells.

Regarding the "excipient only" control: distilled water was used in the present study. None of the bacterial organisms were visibly inhibited by distilled water, relative to the saline growth control, in the "challenge", "outgrowth", or "recovery" plates (i.e., MIC, MBC, and MBEC were all >100%). However, this hypotonic solution did lead to some substantial (and sometimes significant) log10 reductions, relative to the saline growth control, including a reduction of 0.37 (P=0.03) for *S. enterica*, 1.48 (P=0.1) for *E. coli*, 0.67 (P=0.12) for *L. monocytogenes*, and 1.25 (P=0.11) for *E. faecium*. The effects of distilled water were most pronounced for *C. albicans*, yielding an MBEC of just 3.13% water and a log10 reduction of 4.5 (representing a complete loss of viability).

Generally, Gram-positive organisms (*S. aureus*, MRSA, *L. monocytogenes*, and *E. faecium*) were most susceptible to the various hop extracts, but some extracts also showed promise against Gram-negative organisms *S. enterica* and *E. coli* while *P. aeruginosa* and *A. vitis* were not susceptible.

*P. aeruginosa* was not susceptible to any of the tested extracts (i.e., no inhibition in challenge, outgrowth, or MBEC recovery plates and no log10 reductions), possibly reflecting the general robustness of its biofilms.

*A. vitis* was not inhibited in the challenge and outgrowth plates (i.e., MIC and MBC >100%). No growth was observed in the biofilm recovery plate (meaning that no MBEC could be calculated), and no colonies were counted, thus yielding no quantitative log reduction. This leads us to conclude that *A. vitis* forms poor biofilms on the polystyrene pegs used in the present MBEC assay.

*S. aureus* yielded MIC values of 6.25, 3.13, 3.13, and ≤1.56% for M1, W1, N3, and G2 extracts, respectively, with proportionately higher MBC values (25, 12.5, 12.5, and 6.25%) and higher MBEC values (50, 25, 50, and 12.5%). Relative to the saline control, the undiluted extracts all yielded log10 biofilm reductions of 3.65 (representing a complete loss of viability).

MRSA results were similar to those for *S. aureus*.

*C. albicans* was either not susceptible to the hop extracts (based on MIC, MBC, and MBEC values), or was killed simply by distilled water (based on the log reductions).

Overall, the results of this screen indicate that the tested hop extracts are effective against biofilms, particularly, those formed by Gram-positive pathogens like *S. aureus* and *L. monocytogenes*.

Example 5—Growing the Biofilm

The saturated bacterial cultures were diluted 1:10,000 to an approximate density of $10^5$ CFU/mL (10 μL culture +0.99 mL OSB for 1:100, then 200 μL +19.8 mL OSB), except for *A. vitis*, which was used undiluted (O/N culture density of approximately $10^6$ CFU/mL; see below).

The *C. albicans* culture was diluted 1:10 (2 mL+18 mL OSB) for an approximate density of $10^6$ CFU/mL.

The inoculum was poured into a sterile reagent reservoir of the MBEC™ device.

Using a multi-channel pipette, added 150 μL of the inoculum to each well (excluding row H).

Placed the peg lid into the microtiter plate.

NOTE: The volume of inoculum used in this step has been calibrated such that the biofilm covers a surface area that is immersed, entirely, by the volume of antimicrobials used in the challenge plate set up (below).

Placed the device on an orbital shaker in a humidified incubator. Incubated at 110 rpm at 37±1° C. for 16 to 24 hours (26±1° C. for 48 hours for *A. vitis*).

Opened sterile 96-well receiver plates (one per organism tested).

Added 100 μL of OSB to each well of rows B to H.

Added 200 μL of the stock of each test article to the appropriate wells of row A (i.e., article A to wells A1-2, article B to wells A3-4, and so on).

Added 100 μL of the stock of each test article to the appropriate wells of row B (i.e., article A to wells B1-2, article B to wells B3-4, and so on). Mixed the contents by pipetting up and down at least twice.

Added 100 μL of the stock of each test article to the appropriate wells of row C (i.e., article A to wells C1-2, article B to wells C3-4, and so on). Mixed the contents by pipetting up and down at least twice.

After mixing, transferred 100 μL from the wells in row C to the corresponding wells in row D. Mixed the contents by pipetting up and down at least twice.

Transferred 100 μL from row D to row E.

Serially repeated this mix and transfer process down the length of the microtiter plate until reaching row H.

Discarded 100 μL from row H.

Added 100 μL of OSB to rows C-H, yielding 200 μL per well in all wells.

Example 6—Antimicrobial Challenge of the Biofilms

Using sterile 96-well receiver plates, prepared rinse plates (one plate per MBEC lid) containing 200 μL of sterile 0.9% saline per well.

Rinsed planktonic cells from biofilms that had formed on the lid of the MBEC™ device by dipping the lid into the saline for 120 seconds.

Transferred the lid to the challenge plate, and exposed for 24 hours at 37±1° C. (26±1° C. for 24 hours for *A. vitis*) in a humidified incubator.

Example 7—Determination of Planktonic MIC

Removed the lids of the MBEC™ device from the challenge plates and retained both the lid and the challenge plate.

Removed 20 μL from each well of the challenge plate for use as described below.

The challenge plates were incubated at 37±1° C. for 24 hours (26±1° C. for 48 hours for *A. vitis*), before visually scoring for growth. Additionally, an Epoch microtiter plate reader (S/N 240268) was used to obtain optical density measurements at 650 nm (OD650). Clear wells (OD650 less than about 0.1) indicate inhibition following a suitable period of incubation.

Determined the MIC (minimum inhibitory concentration) for each test article for each organism shed from the biofilm during the challenge incubation. The MIC is defined as the minimum concentration that inhibits growth of the organism.

Example 8—Determination of Planktonic MBC

After the specified contact time, 20 μL from each well of the challenge plate was removed (prior to incubating the challenge plate) and placed into the corresponding wells of a fresh 96-well Nunclon plate containing 180 μL of OSM (these were the "outgrowth" plates).

Incubated at 37±1° C. for 24 hours (26±1° C. for 48 hours for *A. vitis*).

MBC results were determined following the 24-hour incubation by +/− growth. Additionally, a microtiter plate reader was used to obtain optical density measurements at 650 nm (OD650). Clear wells (OD650 less than about 0.1) indicate inhibition following a suitable period of incubation.

The MBC (minimum bactericidal concentration) is defined as the minimum concentration that inhibits growth of the organism in this outgrowth plate.

Example 9—Determination of MBEC

Using sterile 96-well receiver plates, prepared rinse plates (one plate per MBEC lid) containing 200 μL of sterile 0.9% saline per well.

Rinsed pegs for 120 seconds.

Using sterile 96-well receiver plates, prepared recovery plates (one per MBEC lid) containing 200 μL per well of the neutralizer/recovery broth.

Transferred the peg lids to the recovery broth.

Transferred the plates (with the pegged lids) into a stainless-steel insert tray, which sat in the water of a bath sonicator.

Sonicated on high for 30 minutes to dislodge surviving biofilm.

NOTE: The vibrations created in the water by the sonicator transfer through the insert tray to actively sonicate the contents of the 96 well recovery plates. (Lindsay, D., von Holy, A., "Evaluation of dislodging methods for laboratory-grown bacterial biofilms," Food Microbiology, Vol 14, No. 4, 1997, pp. 383-390).

Removed the pegged lid and removed 100 μL from each well of row A of this recovery plate for step use below.

Incubated at 37±1° C. for 24 hours (26±1° C. for 48 hours for *A. vitis*).

MBEC results were determined following the 24-hour incubation by +/– growth. Additionally, a microtiter plate reader was used to obtain optical density measurements at 650 nm (OD650). Clear wells (OD650 less than about 0.1) indicate inhibition following a suitable period of incubation.

The MBEC (minimum biofilm eradication concentration) is defined as the minimum concentration that inhibits growth of the organism in this recovery plate.

Example 10—Quantitative Determination of Log10 Reduction in the MBEC Recovery Plate After sonicating the pegged lid in the recovery plate, but before incubating the recovery plate, 100 μL were removed from the "test article" wells (and corresponding growth control wells) of the recovery plate and placed into the wells of row A of a Nunclon 96-well plate. These were serially diluted in saline and spot plate on OSA as described above. NOTE: The wells from Row A of the MBEC recovery plate (corresponding to the highest tested concentrations of each test or control article) were sampled.

Added 100 μL of recovery broth into the sampled wells of the recovery plate to correct the volume back to 200 μL prior to incubating the plate.

Results are shown in Tables 3-6.

Example 11—Quantitative Assessment

This work comprises a quantitative assessment (i.e., log10 reduction assay) of the anti-biofilm activity of hop extracts (Magnum, Willamette, Nugget, and Galena) against three Gram-positive bacteria (*Staphylococcus aureus, Listeria monocytogenes*, and Vancomycin-Resistant *Enterococcus faecium*). The antibiofilm activity was expressed as the Minimum Biofilm Eradication Concentration (MBEC), defined as the lowest concentration of test article yielding a log10 reduction in colony forming units (CFU) of >3 (corresponding to >99.9% reduction). A semi-quantitative assessment (i.e., turbidity assay) of bacteriostatic (MIC) and bactericidal (MBC) effects against planktonic bacteria, as well as anti-biofilm activity (MBEC), was also performed.

The process for high-throughput antimicrobial susceptibility testing uses the MBEC™ assay. This test method specifies the operational parameters required to grow and treat a biofilm in a high throughput screening assay known as the MBEC™ (Minimum Biofilm Eradication Concentration) Assay. The assay device consists of a plastic lid with ninety-six (96) pegs and a corresponding receiver plate with ninety-six (96) individual wells that are filled with 150 μL of inoculum. Biofilm is established on the pegs under batch conditions (i.e., no flow of nutrients into or out of an individual well) with gentle mixing. After 24 hours of growth, the lid, with the biofilm established on the pegs, is rinsed to remove planktonic cells before placing in a new receiver plate for antimicrobial efficacy testing. After a specified contact time, the peg lid is rinsed again, placed in a receiver plate containing a recovery broth, and the entire device is placed in a sonicator to remove the biofilm and disaggregate the clumps. The original challenge plate is incubated, and turbidity is used to assess the MIC. The sonicated recovery plate is incubated, and turbidity is used to assess the MBEC. Samples from each well are then diluted, plated and the viable cells enumerated. The log10 reduction in viable cells is calculated by subtracting the mean log10 density for the treated biofilm from the mean log10 density determined for the untreated controls. Prior to incubating the challenge plate, 20 μL of the challenge medium is removed from each well and placed into fresh medium; after incubating this outgrowth plate, turbidity is used to assess the MBC. The reactor design allows for the simultaneous testing of multiple antimicrobials with replicate samples, making it an efficient screening tool.

Tables 3-6 summarize all the MIC, MBC, and MBEC values obtained from the turbidity assays, as well as the maximum concentration (%) of each test article against which the neutralizing broth was effective:

As can be seen, generally, MBCs were higher than MICs, with MBECs being higher still.

In terms of inhibitory vs bactericidal effects against planktonic bacteria, Willamette extract was the most effective against *S. aureus* (MIC=1.56%; MBC=6.25%) and *L. monocytogenes* (MIC=1.56%, MBC=12.5%), although all 4 hops had similar efficacies against VRE (MIC=25%; MBC=50-100%). MBC is minimal bactericidal concentration, and as such indicates that the extract does kill bacteria and not just inhibit their growth.

All 4 hops had similar efficacies against biofilms (MBEC=50%, 100%, and 100% for *S. aureus, L. monocytogenes*, and VRE, respectively). As will be apparent to those of skill in the art, this shows that the extract does penetrate biofilm to effectively kill bacteria. Consequently, the extract may alternatively be used as an antibacterial adjuvant, that is, a compound that increases the effectiveness of the antibiotic, in this case, by penetrating the biofilm.

Neutralizing recovery broth was generally effective against concentrations of hop extracts at or above the MBEC values.

Neutralizer extract was non-toxic at concentrations far exceeding its used concentration in neutralizing broth.

Example 12—Summary of Quantitative Data

Table 7 summarizes the neutralizer efficacy data for *S. aureus:*

The neutralizing recovery broth was fully effective (i.e., yielded log reductions <1) against concentrations of Magnum, Willamette, Nugget, and Galena as high as 25, 12.5, 12.5, and 25%, respectively.

Table 8 summarizes the neutralizer efficacy data for *L. monocytogenes:*

The neutralizing recovery broth was fully effective (i.e., yielded log reductions <1) against concentrations of Magnum, Willamette, Nugget, and Galena as high as 50%.

Table 9 summarizes the neutralizer efficacy data for VRE:

The neutralizing recovery broth was fully effective (i.e., yielded log reductions <1) against concentrations of Magnum, Willamette, Nugget, and Galena as high as 100%.

Table 10 summarizes the Log10 reduction data for *S. aureus:*

The MBEC (i.e., concentration yielding a log reduction >3) was 6.25, 1.56, 3.13, and 3.13% for Magnum, Willamette, Nugget, and Galena, respectively. As will be appreciated by those of skill in the art, this indicates that Willamette contains the most amount of active ingredients. Consequently, these values may be used to rank the strength of different hop varieties against specific bacteria and/or to look for active compounds across different varieties.

Magnum, Willamette, Nugget, and Galena were completely effective (i.e., no viable CFUs were recovered) at 50, 6.25, 25, and 50%, respectively.

Table 11 summarizes the Log10 reduction data for *L. monocytogenes:*

The MBEC (i.e., concentration yielding a log reduction >3) was 100% for each hop extract, indicating that the extracts can effectively kill biofilm.

Table 12 summarizes the Log10 reduction data for VRE: The MBEC (i.e., concentration yielding a log reduction >3) was >100, 50, >100, and >100% for Magnum, Willamette, Nugget, and Galena, respectively.

As can be seen, MBCs were higher than MICs, with MBECs being higher still. This suggests that the hop extracts tested here are, like other antimicrobial agents, more potent as bacteriostatic agents than as bactericidal agents, and that biofilms are generally less susceptible than planktonic cells to these extracts.

The neutralizing recovery broth is appropriate in terms of efficacy against the tested hop extracts and toxicity against the tested organisms.

As discussed herein, Willamette extract is generally the most potent of the hop extracts tested.

Example 13—Experimental Process for High-Throughput Antimicrobial Susceptibility Testing Using the MBEC™ Assay This test method specifies the operational parameters required to grow and treat a biofilm in a high throughput screening assay known as the MBEC™ (Minimum Biofilm Eradication Concentration) Assay. The assay device consists of a plastic lid with ninety-six (96) pegs and a corresponding receiver plate with ninety-six (96) individual wells that are filled with 150 μL of inoculum. Biofilm is established on the pegs under batch conditions (i.e., no flow of nutrients into or out of an individual well) with gentle mixing. After an appropriate period of growth, the lid—with the biofilm established on the pegs—is rinsed to remove planktonic cells before placing in a new receiver plate for antimicrobial efficacy testing. After a specified contact time, the peg lid is rinsed again, placed in a receiver plate containing a recovery broth, and the entire device is placed in a sonicator to remove the biofilm and disaggregate the clumps. The original challenge plate is incubated and turbidity is used to assess the MIC. The sonicated recovery plate is incubated, and turbidity is used to assess the MBEC. Samples from each well are also diluted, plated, and the viable cells enumerated. The $\log_{10}$ reduction in viable cells is calculated by subtracting the mean $\log_{10}$ density for the treated biofilm from the mean $\log_{10}$ density determined for the untreated controls. Prior to incubating the challenge plate, 20 μL of the challenge medium is removed from each well and placed into fresh medium; after incubating this outgrowth plate, turbidity is used to assess the MBC. The reactor design allows for the simultaneous testing of multiple antimicrobials with replicate samples, making it an efficient screening tool. This standard protocol may be broken into a series of small steps, each of which is detailed in the sections below.

Table 14 summarizes the inoculum densities. The saturated "overnight" (O/N) culture reached an average density of approximately 8 $\log_{10}$ CFU/mL (about $2\times10^8$ CFU/mL). For inoculating the biofilm growth plate, these cultures were diluted to approximately 5 $\log_{10}$ CFU/mL (about $3\times10^5$ CFU/mL).

Table 15 summarizes all the MIC, MBC, and MBEC values obtained from the turbidity assays, as well as the maximum concentration (%) of each test article against which the neutralizing broth was effective.

Table 16 the neutralizer efficacy results for *P. larvae*. The neutralizing recovery broth was fully effective (i.e., yielded log reductions <1) against 1.56% Magnum, and partially effective against 6.25% Willamette, but was otherwise ineffective against the tested concentrations of hop extracts.

Table 17 summarizes the $\text{Log}_{10}$ reduction data. Consistent with the discussed above, for all four tested hop extracts, the MBEC (i.e., concentration yielding a log reduction >3) was below the minimum observable level (i.e., less than the minimum concentration tested), indicating that *P. larvae* biofilms are extremely sensitive to all four hop extracts.

Table 18 summarizes the turbidity and plate count assays shown in Table 4. These are the results of the MBEC™ assay covering both planktonic cell MIC (bacteriostatic concentration) and MBC (bactericidal concentration), as well as biofilm eradication in MBEC. A $\log_{10}$ reduction of >3 indicates complete eradication at 99.99% efficiency. The results are fairly consistent with a P-value of 0.12.

Table 19 is a succinct summary of the results in table 5 with the inclusion of neutralizer efficiency as well.

Tables 15 and 18 demonstrate the efficacy of the test articles against *P. larvae* in both planktonic and biofilm conditions. All test articles were able to achieve a $\log_{10}$ reduction of >3 indicating a strong affect against the organism.

Moreover, at every tested concentration, each hop extract yielded the maximum achievable log reduction—that is, no colonies were recovered from pegs treated with hops, so the reported log reductions are limited by the number of colonies recovered from the corresponding saline-treated pegs.

Example 14—Quantitative Assesment of the Antimicrobial Efficacy of Hop Extracts Against a Spore-Enriched Preparation of *P. Larvae*

In this Quantitative Carrier Test (QCT), the test organism was suspended in a tripartite soil load and dried onto the surface of a plastic carrier before challenging for 24 hours at 37° C. with a broad range of hops concentrations. A neutralizing broth was then added, and the mixture was serially diluted and plated to enumerate viable colony forming units per milliliter (CFU/mL).

A summary of the data is shown in Table 20.

The neutralizing recovery broth was only effective against the lowest concentrations of hops tested here (i.e., 1% v/v).

The data indicate that all four tested hops have antimicrobial efficacy against a spore-enriched *P. larvae* preparation, and that Willamette and Nugget are the most potent overall, achieving "maximum kill" at just 1% v/v.

The purpose of this study was to determine the potency of Magnum, Willamette, Nugget, and Galena hop extracts against *P. larvae* spores.

Two methods of spore enrichment (Heat and Alcohol) were compared.

The quantitative carrier test (QCT) aimed to assess the sporicidal activities of the hops against *P. larvae* spores dried onto a carrier in the presence of an organic soil load ("worst case scenario" for the hops).

The efficacy of the neutralizing recovery broth against each tested concentration of hop extracts was also assessed, as was its toxicity against the spores.

A broad concentration range of the hop extracts (100, 10, and 1% v/v) was tested for a single contact time of 24 hours.

Contact Time: 24 hours.

Contact Temperature: 37±1° C.

Carriers: The inside bottom surface of polystyrene 96 well flat bottom plates (Catalogue ref 167008, Nunc, Denmark) were used as the carrier surface for the quantitative carrier test.

Soil Load: For inoculation of the carriers, the test organisms were first suspended in a tripartite soil load: 50 µL of bovine serum albumin, 200 µL of mucin and 70 µL of Tryptone was added to 680 µL of the microbial suspension. This soil load mixture contained a level of protein roughly equal to that in 5% bovine serum.

Universal Neutralizer: For research applications it is appropriate to employ a neutralizing agent for determination of minimum bactericidal and fungicidal concentrations. These agents reduce toxicity from the carry-over of biologically active compounds from challenge to recovery media. As examples, it is possible to use β-lactamase to neutralize penicillin, or L-cysteine to neutralize heavy metal cations.

Preparation: 1.0 g L-Histidine; 1.0 g L-Cysteine; 2.0 g Reduced glutathione

Made up to 20 mL in double distilled water. Passed through a syringe with a 0.20 µm filter to sterilize. This solution ("neutralizer supplement") was stored at–20° C. in 0.5-mL aliquots.

Made up 1 litre of Mueller Hinton Broth (MHB), supplemented with 20.0 g per litre of saponin and 10.0 g per litre of Tween-80 prior to autoclaving. Adjusted with dilute NaOH to the correct pH (7.0±0.2 at 20° C.). Autoclaved.

Prepared 100 mg/mL stocks of cations: dissolved 10 g of $CaCl2$ in 100 mL $H_2O$ and 10 g of $MgCl_2$ in 100 mL $H_2O$: passed through a syringe with a 0.20 µm filter to sterilize. After autoclaving the surfactant-supplemented MHB, added 2 mL $CaCl_2$ (20 mg/L final) and 1 mL $MgCl_2$ (10 mg/L final) to produce cation adjusted MHB (CAMHB).

On the day of testing, added 500 µL of the universal neutralizer supplement solution to every 20 mL of the CAMHB.

Preparation

Soil Load Components:

Dissolved 0.5 g tryptone in 10 mL PBS.

Dissolved 0.5 g bovine serum albumin (BSA) in 10 mL PBS.

Dissolved 0.04 g mucin in 10 mL of PBS.

Prepared the solutions separately and sterilized by passage through a 0.22 µm pore diameter membrane filter. Aliquoted and stored at 4° C. (used within 3 months).

Test Articles: On the day of the experiment, thawed the undiluted test article stocks (=100%) and performed a serial (10-fold) dilution of each test article (i.e., 100 µL hop extract plus 900 µL saline) to yield 10% v/v and 1% v/v.

Culture/Inoculum Preparation

Using a cryogenic stock (at–70° C.), streaked out a first sub-culture of the organisms on OSA.

Incubated at 37±1° C./5% $CO_2$ for 48 hours and stored the plate wrapped in parafilm at 4° C.

From the first sub-culture, streaked out a second sub-culture on OSA. Incubated at 37±1° C./5% $CO_2$ for 48 hours. The second sub-culture was used within 24 hours starting from the time it was first removed from incubation.

Using the second sub-culture, aseptically removed 1-5 isolated colonies from the OSA plate and inoculated 5 mL of OSB in a 50-mL screw-top tube (or similar).

Placed the culture on an orbital shaker in a humidified incubator; incubated at 200 rpm at 37±1° C. for 24 hours. This yielded a culture of approximately $5\times10^6$ CFU/mL.

Moved 100 µL of the saturated O/N culture into each of three wells (in row A) of a 96-well plate for an O/N inoculum check:

Added 180 µL of sterile 0.9% saline to the remaining rows.

Serially diluted with a multichannel pipettor (100-10-7) by transferring 20 µL down each of the 8 rows for each plate.

Mixed the contents by pipetting up and down at least 3 times. After mixing each row, discarded the pipette tips. Using fresh tips, continued the dilution procedure.

Using a single channel pipettor, removed 20 µL from each well and plated on OSA plates5. Used a fresh tip for each well. NOTE: One OSA plate was used for each dilution series by dividing individual plates into eight pie-shaped sections and labelling the sections $10^0$-$10^{-7}$.

Incubated the agar plates at 37±1° C./5% $CO_2$ for 48 hours and enumerated colonies.

Spore Preparation

Diluted the O/N culture (from 9.5) 100-fold (i.e., 100 µL of O/N plus 900 µL saline) for ~$5\times10^4$ CFU/mL.

Spread 100 µL of the ~$10^4$ CFU/mL suspension onto each of 20 TSA plates.

NOTE: This step intentionally used TSA instead of BHIA+Thiamine.

Incubated the TSA plates for 8 days at 37±1° C./5% $CO^2$.

Doused each plate with 5 mL of cold (4° C.) sterile dH2O and held for 15 minutes.

Using inoculating loops or cell scrapers, colonies were gently scraped from the surface of the plate and into suspension.

Combined the suspension from five plates into each of four 50-mL screw-top tubes (~25 mL per tube); used sterile $dH_2O$ to balance tubes within 0.01 g of one another.

Centrifuged at 4816×g for 20 minutes (12° C.) and discarded the supernatant.

Resuspended each pellet in 12.5 mL cold sterile $dH_2O$ and consolidated into two 50-mL tubes (25 mL per tube).

Centrifuged again and resuspended each pellet in 25 mL cold sterile $dH_2O$.

Centrifuged once more.

Killed any remaining vegetative or germinated cells by each of the following methods:

Resuspended one pellet in 2.5 mL of 80% ethanol and incubated at room temperature for 15 minutes. Removed the spores from ethanol by centrifuging (4816×g for 20 minutes at 12° C.), discarding the supernatant, and washing three more times with $dH_2O$ (final resuspension volume: 2.5 mL$dH_2O$). Stored at 4° C.

Resuspended the other pellet in 2.5 mL of sterile $dH_2O$ and heated in a 65° C. water bath for 15 minutes before washing and resuspending as above. Stored at 4° C.

Enumerated viable spores:

Moved 100 µL of each spore stock into each of each of three wells (in row A) of a 96-well plate (prepared two identical plates).

Heated one of the plates to 65±2° C. for 15 minutes to kill any germinated bacteria; the other plate proceeded directly to the next step as a "total viability" control.

Removed plate 1 from heat and added 180 µL of sterile 0.9% saline to the remaining rows (i.e., B to H) of both plates.

Serially diluted with a multichannel pipettor ($10^0$-$10^{-7}$) by transferring 20 µL down each of the 8 rows for each plate. Mixed the contents by pipetting up and down at least 3 times. After mixing each row, discarded the pipette tips. Using fresh tips, continued the dilution procedure.

Using a single channel pipettor, removed 20 µL from each well and plated on OSA plates. Used a fresh tip for each well. NOTE: One OSA plate was used for each dilution series by dividing individual plates into eight pie-shaped sections and labelling the sections $10^0$-$10^{-7}$.

Incubated the agar plates at 37±1° C./5% $CO_2$ for 48-96 hours and enumerated colonies.

Quantitative Carrier Test

To obtain a 1000 µL Soil Load inoculum: Mixed 680 µL of spore suspension with a mixture of 50, 200, and 70 µL of BSA, mucin, and tryptone stock solutions, respectively.

Opened the sterile package of flat-bottom 96-well plates (1 per test article).

Using a micro pipette, added 10 µL of the soil load inoculum to each well utilized in row A.

Allowed the inoculum to dry at room temperature by first holding the carriers in a biosafety cabinet for approximately 1-2 hours with the lid askew.

When the soil load inoculum had dried, added 100 µL of the properly prepared test product or saline to the appropriate wells of row A of the test plate.

Mixed the contents by pipetting up and down at least 3 times.

Allowed the test to stand at the desired temperature (37° C.) for 24 hours in a humidified incubator.

After the 24 hours, added 100 µL of neutralizer using a multichannel pipettor.

Mixed the contents by pipetting up and down at least 3 times.

Conclusions and Discussion

Heat-resistant CFU/mL recovery—intended here as a measure of spore viability—was similar for the two spore preparation methods (Heat vs Ethanol) and similar to "total" viability, suggesting a high purity of spores (i.e., few vegetative survivors) for either enrichment method.

Anecdotally, the high overall efficiency of spore enrichment (relative to vegetative survivors) is supported by the heterogeneity in size of the colonies obtained, with relatively few "large" colonies (which grew to normal size in the typical 48-hours and thus likely represent vegetative cells) versus the smaller colonies (which took 96-hours to grow to normal size and thus likely represent spores that required additional germination time).

The inoculum density of the spore suspension was about 4.6 $\log_{10}$ CFU/mL, which was identical to its density when first prepared, indicating no loss of viability after approximately 1 week at 4° C. in distilled water and consistent with spore versus vegetative cell behaviour.

The density increased slightly (but statistically significantly; P=0.0001) to 5.8 $\log_{10}$ CFU/mL for the soil load inoculum. Given the mock challenge time of 24 hours at 37° C. used here, it is likely that some germination (or outgrowth of any surviving vegetative cells) occurred in this carbon-rich soil load.

The neutralizer toxicity test (i.e., 10 µL of spore suspension incubated with 200 µL of neutralizing broth for 24 hours at 37° C.) yielded a similar (but statistically significantly higher) density to the spore suspension (4.8 versus 4.6 $\log_{10}$ CFU/mL; P=0.0202). Accounting for the dilution, the expected density of this inoculum was only 3.3 $\log_{10}$ CFU/ mL. Like the soil load check above, this suggests that some germination (or possibly vegetative growth) occurred in this carbon rich neutralizing broth. In any case, the neutralizing broth was not toxic.

In the neutralizer efficacy tests, the saline-treated growth controls yielded between approximately 3.5 to 3.8 log10 CFU/mL. For all four hops, zero colonies were recovered for the 100% or 10% concentrations (corresponding to statistically significant $\log_{10}$ reductions of 3.5 to 3.8), indicating a failure of the neutralizer against these hops concentrations but confirming their efficacy against P. larvae spores in suspension. Colonies were recovered for the 1% concentration of all four hops, yielding statistically insignificant $\log_{10}$ reductions of about 1 for Magnum and Willamette and significant $\log_{10}$ reductions of <1 for Nugget and Gelena; together with the potency of most hops at 1% in the absence of neutralizer, this suggests partial efficacy of the neutralizer against these low hop concentrations.

Quantitative Carrier Test

The saline-treated growth controls yielded between approximately 3.4 to 3.7 $\log_{10}$ CFU/mL. For all four hops, zero colonies were recovered for the 100% or 10% concentrations (corresponding to statistically significant $\log_{10}$ reductions of 3.4 to 3.7), indicating their efficacy against P. larvae spores in soil load. Magnum at 1% yielded a statistically insignificant $\log_{10}$ reduction of only 1.2, indicating a lack of potency at this low concentration. Galena at 1% yielded a statistically significant (P=0.006) $\log_{10}$ reduction of 3.1, indicating almost full potency at this low concentration (Table 20). Both Willamette and Nugget displayed full potency at 1%. Together, these data confirm that all four hops have antimicrobial efficacy against spore-enriched P. larvae preparations, and that Willamette and Nugget are the most potent overall, achieving "maximum kill" at just 1% v/v.

Example 15—Mortality of Varroa Mites

In this example, 0.75 ml of extract was used. Mites were exposed to the extract for 4 hours, transferred to a clean vial, and then assessed for mortality at 24 hours. The data are shown in Table 23.

A one-way ANOVA on Trial 2 data did find a significant effect of concentration (F5,14=3.50; p=0.029), and a post-hoc Fisher test found that the 100% and 200% concentrations resulted in significantly more mite mortality than control treatments (p=0.034 and p=0.003, respectively). The 200% concentration also had significantly more mite mortality than the 25% concentration (p=0.008).

Example 16—M. Plutonius

MIC, MBC and MBEC values were determined for M. plutonius as described above.

For example, for inoculating the biofilm growth plate, the saturated culture was diluted to yield 5.75 $\log_{10}$ CFU/mL (about $5.67 \times 10^5$ CFU/mL).

Shown in Table 24 are the MIC, MBC, and MBEC values obtained from the turbidity assays, as well as the maximum concentration (%) of each test article against which the neutralizing broth was effective:

The MIC for saline was 100%, indicating that the 24-hour challenge with undiluted saline was sufficient to inhibit planktonic growth of M. plutonius. The MBC and MBEC for saline were both >100%. Similar results were obtained for S. aureus, L. monocytogenes, and VRE, discussed above.

Neutralizing recovery broth was generally effective against concentrations of extracts at their MIC, MBC, or MBEC values.

Neutralizing broth was non-toxic (i.e., yielded turbidity) at concentrations as high as 100%.

For NRCS-019 and -014, the MIC and MBC were both 10%, indicating that a 10-fold dilution of either extract was bactericidal against M. plutonius.

Very few CFUs were recovered from any of the positive growth controls (with the highest log10 CFU/peg recovery being just 1.39), indicating a failure of M. plutonius to form a robust biofilm under the conditions of this assay. Consequently, no log reduction exceeding 3 (i.e., >99.9% reduction) was observed for any tested concentration of NRCS-019 or -014.

In summary, each tested extract was bactericidal against planktonic *M. plutonius* at a concentration as low as 10%. While the extracts were more potent against *P. larvae* (discussed above), these results confirm that the extracts possess antimicrobial activity against multiple honeybee pathogens, and against other Gram-positive pathogens (discussed above).

While the preferred embodiments of the invention have been described above, it will be recognized and understood that various modifications may be made therein, and the appended claims are intended to cover all such modifications which may fall within the spirit and scope of the invention.

TABLE 1

MIC Results

| | S. aureus | MRSA | B. subtilis | VRE | L. monocytogenes | C. acnes | S. pyrogenes | S. typhimurium | E. coli |
|---|---|---|---|---|---|---|---|---|---|
| Brewers Gold | 0.4 | 0.4 | 0.4 | 1.6 | 0.4 | 0.1 | 100 | 50 | 50 |
| Cascade | 0.1 | 0.2 | 0.2 | 0.8 | 0.1 | 0.1 | 100 | 12.5 | 50 |
| Cashmere | 0.05 | 0.1 | 0.2 | 0.1 | 0.05 | 0.1 | 100 | 25 | 50 |
| Centennial | 0.4 | 0.4 | 0.4 | 1.6 | 0.4 | 0.1 | 100 | 50 | 50 |
| Challenger | 0.2 | 0.2 | 0.4 | 0.8 | 0.1 | 0.05 | 100 | 12.5 | 100 |
| Chinook | 0.2 | 0.4 | 0.4 | 1.6 | 0.2 | 0.05 | 100 | 25 | 50 |
| Hallertau | 0.1 | 0.2 | 0.2 | 0.8 | 0.1 | 0.05 | 100 | 12.5 | 50 |
| Magnum | 0.1 | 0.1 | 0.4 | 0.8 | 0.1 | 0.05 | 100 | 50 | 100 |
| Northern Brew | 0.1 | 0.2 | 0.2 | 0.4 | 0.1 | 0.1 | 100 | 50 | 100 |
| Nugget | 0.1 | 0.2 | 0.2 | 0.8 | 0.1 | 0.05 | 100 | 50 | 50 |
| Saaz | 0.4 | 0.4 | 0.8 | 1.6 | 0.4 | 0.1 | 100 | 50 | 50 |
| Willamette | 0.05 | 0.05 | 0.1 | 0.2 | 0.05 | 0.05 | 100 | 25 | 50 |
| Crystal | 0.4 | 0.4 | 0.4 | 1.6 | 0.4 | 0.1 | 100 | 0 | 50 |
| Galena | 0.05 | 0.2 | 0.05 | 0.2 | 0.05 | 0.05 | 100 | 50 | 50 |
| Wild-Hop | 0.2 | 0.4 | 0.4 | 1.6 | 0.2 | 0.05 | 100 | 0 | 50 |

\* Numbers obtained through Resazurin assay. Optical density indicated no effect
All numbers represented as %

TABLE 1

MIC Results

| | S. aureus | MRSA | B. subtilis | VRE | L. monocytogenes | C. acnes | S. pyrogenes | S. typhimurium | E. coli |
|---|---|---|---|---|---|---|---|---|---|
| Brewers Gold | 0.4 | 0.4 | 0.4 | 1.6 | 0.4 | 0.1 | 100 | 50 | 50 |
| Cascade | 0.1 | 0.2 | 0.2 | 0.8 | 0.1 | 0.1 | 100 | 12.5 | 50 |
| Cashmere | 0.05 | 0.1 | 0.2 | 0.1 | 0.05 | 0.1 | 100 | 25 | 50 |
| Centennial | 0.4 | 0.4 | 0.4 | 1.6 | 0.4 | 0.1 | 100 | 50 | 50 |
| Challenger | 0.2 | 0.2 | 0.4 | 0.8 | 0.1 | 0.05 | 100 | 12.5 | 100 |
| Chinook | 0.2 | 0.4 | 0.4 | 1.6 | 0.2 | 0.05 | 100 | 25 | 50 |
| Hallertau | 0.1 | 0.2 | 0.2 | 0.8 | 0.1 | 0.05 | 100 | 12.5 | 50 |
| Magnum | 0.1 | 0.1 | 0.4 | 0.8 | 0.1 | 0.05 | 100 | 50 | 100 |
| Northern Brew | 0.1 | 0.2 | 0.2 | 0.4 | 0.1 | 0.1 | 100 | 50 | 100 |
| Nugget | 0.1 | 0.2 | 0.2 | 0.8 | 0.1 | 0.05 | 100 | 50 | 50 |
| Saaz | 0.4 | 0.4 | 0.8 | 1.6 | 0.4 | 0.1 | 100 | 50 | 50 |
| Willamette | 0.05 | 0.05 | 0.1 | 0.2 | 0.05 | 0.05 | 100 | 25 | 50 |
| Crystal | 0.4 | 0.4 | 0.4 | 1.6 | 0.4 | 0.1 | 100 | 0 | 50 |
| Galena | 0.05 | 0.2 | 0.05 | 0.2 | 0.05 | 0.05 | 100 | 50 | 50 |
| Wild-Hop | 0.2 | 0.4 | 0.4 | 1.6 | 0.2 | 0.05 | 100 | 0 | 50 |

\* Numbers obtained through Resazurin assay. Optical density indicated no effect
All numbers represented as %

TABLE 2

Zones of inhibition

| | S. aureus | MRSA | B. subtilis | VRE | L. monocytogenes | C. acnes |
|---|---|---|---|---|---|---|
| Brewers Gold | 20 | 21 | 15 | 11 | 16 | 29 |
| Cascade | 21 | 23 | 16 | 12 | 19 | 34 |
| Cashmere | 20 | 23 | 18 | 13 | 15 | 33 |
| Centennial | 18 | 21 | 15 | 11 | 15 | 37 |

34

TABLE 2-continued

Zones of inhibition

| | S. aureus | MRSA | B. subtilis | VRE | L. monocytogenes | C. acnes |
|---|---|---|---|---|---|---|
| Challenger | 22 | 23 | 14 | 9 | 14 | 34 |
| Chinook | 19 | 21 | 16 | 9 | 16 | 32 |
| Hallertau | 22 | 24 | 17 | 12 | 20 | 34 |
| Magnum | 21 | 24 | 16 | 10 | 18 | 36 |
| Northern Brew | 19 | 23 | 13 | 12 | 18 | 38 |

TABLE 2-continued

Zones of inhibition

| | S. aureus | MRSA | B. subtilis | VRE | L. monocytogenes | C. acnes |
|---|---|---|---|---|---|---|
| Nugget | 19 | 20 | 18 | 10 | 16 | 31 |
| Saaz | 18 | 18 | 13 | 9 | 18 | 31 |
| Willamette | 21 | 23 | 19 | 13 | 17 | 37 |
| Crystal | 18 | 20 | 9 | 10 | 16 | 37 |

TABLE 2-continued

| | | | | | | |
|---|---|---|---|---|---|---|
| | Zones of inhibition | | | | | |
| | S. aureus | MRSA | B. subtilis | VRE | L. monocytogenes | C. acnes |
| Galena | 20 | 25 | 19 | 11 | 20 | 39 |
| Wild-Hop | 20 | 23 | 14 | 11 | 19 | 30 |

All numbers represented as mm, no inhibition of *S. pyogenes*, *S. typhimurium* or *E. coli*.

TABLE 3

MIC, MBC, and MBEC values for the various test articles and organisms are reported as percentages (where "100%" corresponds to the undiluted test article).

| Organism | Test Article | MIC (%) | MBC (%) | MBEC (%) |
|---|---|---|---|---|
| *P. aeruginosa* | A (M1 Hop Extract) | >100 | >100 | >100 |
| | B (W1 Hop Extract) | >100 | >100 | >100 |
| | C (N3 Hop Extract) | >100 | >100 | >100 |
| | D (G2 Hop Extract) | >100 | >100 | >100 |
| | E (Distilled Water) | >100 | >100 | >100 |
| | GC (Saline) | >100 | >100 | >100 |
| *S. enterica* | A (M1 Hop Extract) | >100 | >100 | >100 |
| *s. choleraesuis* | B (W1 Hop Extract) | >100 | >100 | >100 |
| | C (N3 Hop Extract) | >100 | >100 | >100 |
| | D (G2 Hop Extract) | >100 | >100 | >100 |
| | E (Distilled Water) | >100 | >100 | >100 |
| | GC (Saline) | >100 | >100 | >100 |
| *E. coli* | A (M1 Hop Extract) | >100 | >100 | >100 |
| | B (W1 Hop Extract) | >100 | >100 | >100 |
| | C (N3 Hop Extract) | >100 | >100 | >100 |
| | D (G2 Hop Extract) | >100 | >100 | >100 |
| | E (Distilled Water) | >100 | >100 | >100 |
| | GC (Saline) | >100 | >100 | >100 |
| *A. vitis* | A (M1 Hop Extract) | >100 | >100 | — |
| | B (W1 Hop Extract) | >100 | >100 | — |

TABLE 3-continued

MIC, MBC, and MBEC values for the various test articles and organisms are reported as percentages (where "100%" corresponds to the undiluted test article).

| Organism | Test Article | MIC (%) | MBC (%) | MBEC (%) |
|---|---|---|---|---|
| | C (N3 Hop Extract) | >100 | >100 | — |
| | D (G2 Hop Extract) | >100 | >100 | — |
| | E (Distilled Water) | >100 | >100 | — |
| | GC (Saline) | >100 | >100 | — |
| *S. aureus* | A (M1 Hop Extract) | 6.25 | 25 | 50 |
| | B (W1 Hop Extract) | 3.13 | 12.5 | 25 |
| | C (N3 Hop Extract) | 3.13 | 12.5 | 50 |
| | D (G2 Hop Extract) | <1.56 | 6.25 | 12.5 |
| | E (Distilled Water) | >100 | >100 | >100 |
| | GC (Saline) | >100 | >100 | >100 |
| MRSA | A (M1 Hop Extract) | 6.25 | 6.25 | 12.5 |
| | B (W1 Hop Extract) | 3.13 | 3.13 | 6.25 |
| | C (N3 Hop Extract) | 3.13 | 3.13 | 3.13 |
| | D (G2 Hop Extract) | <1.56 | <1.56 | <1.56 |
| | E (Distilled Water) | >100 | >100 | >100 |
| | GC (Saline) | >100 | >100 | >100 |
| *L. monocytogenes* | A (M1 Hop Extract) | 3.13 | 25 | 100 |
| | B (W1 Hop Extract) | 3.13 | 25 | 100 |
| | C (N3 Hop Extract) | 3.13 | 25 | 100 |
| | D (G2 Hop Extract) | <1.56 | 12.5 | 100 |
| | E (Distilled Water) | >100 | >100 | >100 |
| | GC (Saline) | >100 | >100 | >100 |
| *E. faecium* (VRE) | A (M1 Hop Extract) | 6.25 | 100 | 100 |
| | B (W1 Hop Extract) | 6.25 | 100 | 100 |
| | C (N3 Hop Extract) | 6.25 | 100 | >100 |
| | D (G2 Hop Extract) | 3.13 | 50 | 100 |
| | E (Distilled Water) | >100 | >100 | >100 |
| | GC (Saline) | >100 | >100 | >100 |
| *C. albicans* | A (M1 Hop Extract) | >100 | >100 | >100 |
| | B (W1 Hop Extract) | >100 | >100 | 100 |
| | C (N3 Hop Extract) | >100 | >100 | 100 |
| | D (G2 Hop Extract) | >100 | >100 | >100 |
| | E (Distilled Water) | >100 | >100 | 3.13 |

TABLE 4

Summary of Quantitative Data.
Log reductions.

| Organism | Treatment | Mean Log10 CFU/mL | SD | Log10 Reduction | P* | % Red |
|---|---|---|---|---|---|---|
| *P. aeruginosa* | A (M1 Hop Extract) | 5.70 | 0.06 | −1.05 | 0.01 | −1000 |
| | B (W1 Hop Extract) | 5.33 | 0.30 | −0.69 | 0.10 | −386.2 |
| | C (N3 Hop Extract) | 5.20 | 0.28 | −0.56 | 0.13 | −260.4 |
| | D (G2 Hop Extract) | 5.42 | 0.17 | −0.78 | 0.04 | −503.0 |
| | E (Distilled Water) | 4.73 | 0.35 | −0.09 | 0.78 | −21.68 |
| | GC (Saline) | 4.64 | 0.14 | — | — | — |
| *S. enterica* | A (M1 Hop Extract) | 1.02 | 1.29 | 1.33 | 0.28 | 95.29 |
| | B (W1 Hop Extract) | 1.73 | 0.03 | 0.62 | 0.01 | 76.21 |
| | C (N3 Hop Extract) | 3.05 | 0.01 | −0.70 | 0.00 | −401.2 |
| | D (G2 Hop Extract) | 2.83 | 0.24 | −0.48 | 0.12 | −199.1 |
| | E (Distilled Water) | 1.98 | 0.06 | 0.37 | 0.03 | 57.49 |
| | GC (Saline) | 2.35 | 0.07 | — | — | — |
| *E. coli* | A (M1 Hop Extract) | 1.84 | 0.19 | 2.42 | 0.02 | 99.62 |
| | B (W1 Hop Extract) | 3.26 | 0.73 | 1.01 | 0.25 | 90.14 |
| | C (N3 Hop Extract) | 1.94 | 0.33 | 2.32 | 0.03 | 99.52 |
| | D (G2 Hop Extract) | 0.85 | 1.21 | 3.41 | 0.07 | 99.96 |
| | E (Distilled Water) | 2.79 | 0.55 | 1.48 | 0.10 | 96.67 |
| | GC (Saline) | 4.27 | 0.48 | — | — | — |
| *A. vitis* | A (M1 Hop Extract) | 0.00 | 0.00 | — | — | — |
| | B (W1 Hop Extract) | 0.00 | 0.00 | — | — | — |
| | C (N3 Hop Extract) | 0.00 | 0.00 | — | — | — |
| | D (G2 Hop Extract) | 0.00 | 0.00 | — | — | — |
| | E (Distilled Water) | 0.00 | 0.00 | — | — | — |
| | GC (Saline) | 0.00 | 0.00 | — | — | — |
| *S. aureus* | A (M1 Hop Extract) | 0.00 | 0.00 | 3.65 | 0.00 | 99.98 |
| | B (W1 Hop Extract) | 0.00 | 0.00 | 3.65 | 0.00 | 99.98 |
| | C (N3 Hop Extract) | 0.00 | 0.00 | 3.65 | 0.00 | 99.98 |
| | D (G2 Hop Extract) | 0.00 | 0.00 | 3.65 | 0.00 | 99.98 |

TABLE 4-continued

Summary of Quantitative Data.
Log reductions.

| Organism | Treatment | Mean Log10 CFU/mL | SD | Log10 Reduction | P* | % Red |
|---|---|---|---|---|---|---|
| | E (Distilled Water) | 3.65 | 0.00 | −0.01 | 0.97 | −1.900 |
| | GC (Saline) | 3.65 | 0.24 | — | — | — |
| MRSA | A (M1 Hop Extract) | 0.00 | 0.00 | 8.45 | 0.00 | >99.99 |
| | B (W1 Hop Extract) | 0.00 | 0.00 | 8.45 | 0.00 | >99.99 |
| | C (N3 Hop Extract) | 0.00 | 0.00 | 8.45 | 0.00 | >99.99 |
| | D (G2 Hop Extract) | 0.00 | 0.00 | 8.45 | 0.00 | >99.99 |
| | E (Distilled Water) | 8.35 | 0.07 | 0.10 | 0.58 | 20.94 |
| | GC (Saline) | 8.45 | 0.21 | — | — | — |
| L. monocytogenes | A (M1 Hop Extract) | 0.00 | 0.00 | 3.31 | 0.00 | 99.95 |
| | B (W1 Hop Extract) | 0.00 | 0.00 | 3.31 | 0.00 | 99.95 |
| | C (N3 Hop Extract) | 0.00 | 0.00 | 3.31 | 0.00 | 99.95 |
| | D (G2 Hop Extract) | 0.00 | 0.00 | 3.31 | 0.00 | 99.95 |
| | E (Distilled Water) | 2.64 | 0.34 | 0.67 | 0.12 | 78.74 |
| | GC (Saline) | 3.31 | 0.11 | — | — | — |
| E. faecium (VRE) | A (M1 Hop Extract) | 0.00 | 0.00 | 2.72 | 0.00 | 99.81 |
| | B (W1 Hop Extract) | 0.00 | 0.00 | 2.72 | 0.00 | 99.81 |
| | C (N3 Hop Extract) | 0.00 | 0.00 | 2.72 | 0.00 | 99.81 |
| | D (G2 Hop Extract) | 0.00 | 0.00 | 2.72 | 0.00 | 99.81 |
| | E (Distilled Water) | 1.47 | 0.61 | 1.25 | 0.11 | 94.37 |
| | GC (Saline) | 2.72 | 0.17 | — | — | — |
| C. albicans | A (M1 Hop Extract) | 1.15 | 1.63 | 3.35 | 0.10 | 99.96 |
| | B (W1 Hop Extract) | 0.00 | 0.00 | 4.50 | 0.00 | >99.99 |
| | C (N3 Hop Extract) | 0.00 | 0.00 | 4.50 | 0.00 | >99.99 |
| | D (G2 Hop Extract) | 0.39 | 0.55 | 4.11 | 0.01 | 99.99 |
| | E (Distilled Water) | 0.00 | 0.00 | 4.50 | 0.00 | >99.99 |
| | GC (Saline) | 4.50 | 0.14 | — | — | — |

*P-values were determined by unpaired, 2-tailed T-test. As the sample size was only 2 for each treatment condition, P-values should be interpreted cautiously.

TABLE 5

Summary of Main Findings

| Organism | Test Article | Turbidity Assay | | | Quantitative (Plate Count) Assay | | | |
|---|---|---|---|---|---|---|---|---|
| | | MIC (%) | MBC (%) | MBEC (%) | MBEC (%) | Log10 Reduction | P (vs GC) | % Reduction |
| S. aureus | A (Magnum) | 6.25 | 12.5 | 50 | 6.25 | 4.96 | 0.01 | 100.00 |
| | B (Willamette) | 1.56 | 6.25 | 50 | 1.56 | 4.95 | 0.00 | 100.00 |
| | C (Nugget) | 3.13 | 12.5 | 50 | 3.13 | 5.49 | 0.00 | 100.00 |
| | D (Galena) | 3.13 | 12.5 | 50 | 3.13 | 3.73 | 0.04 | 99.98 |
| | GC (Saline) | >100 | >100 | >100 | >100 | — | — | — |
| L. monocytogenes | A (Magnum) | 3.13 | 25 | 100 | 100 | 3.35 | 0.00 | 99.96 |
| | B (Willamette) | 1.56 | 12.5 | >100 | 100 | 3.35 | 0.00 | 99.96 |
| | C (Nugget) | 3.13 | 12.5 | 100 | 100 | 3.37 | 0.00 | 99.96 |
| | D (Galena) | 3.13 | 25 | 100 | 100 | 3.37 | 0.00 | 99.96 |
| | GC (Saline) | >100 | >100 | >100 | >100 | — | — | — |
| E. faecium (VRE) | A (Magnum) | 25 | 100 | 100 | >100 | 2.46 | 0.00 | 99.65 |
| | B (Willamette) | 25 | 50 | 100 | 50 | 3.49 | 0.00 | 99.97 |
| | C (Nugget) | 25 | 50 | 100 | >100 | 2.71 | 0.00 | 99.81 |
| | D (Galena) | 25 | 50 | 100 | >100 | 2.71 | 0.00 | 99.81 |
| | GC (Saline) | >100 | >100 | >100 | >100 | — | — | — |

Overall, MBEC results from the turbidity-based assays are similar to those previously observed (see 21063-001).

As expected, and consistent with previous work (see 21063-001), MBCs were higher than MICs, with MBECs being higher still. This suggests that the hop extracts tested here are—like other antimicrobial agents—more potent as bacteriostatic agents than as bactericidal agents, and that biofilms are generally less susceptible than planktonic cells to these extracts.

The neutralizing recovery broth is appropriate in terms of efficacy against the tested hop extracts and toxicity against the tested organisms.

Willamette extract is generally the most potent of the hop extracts tested.

TABLE 6

Summary of Data from the Visual Turbidity Assays. MIC, MBC, and MBEC values for the various test articles and organisms are reported as percentages (where "100%" corresponds to the undiluted test article).

| Organism | Test Article | MIC (%) | MBC (%) | MBEC (%) | Neut. Effective against: (Max. % of test article)* |
|---|---|---|---|---|---|
| S. aureus | A (Magnum) | 6.25 | 12.5 | 50 | 50 |
| | B (Willamette) | 1.56 | 6.25 | 50 | 50 |
| | C (Nugget) | 3.13 | 12.5 | 50 | 50 |
| | D (Galena) | 3.13 | 12.5 | 50 | 50 |
| | GC (Saline) | >100 | >100 | >100 | N/A |
| L. monocytogenes | A (Magnum) | 3.13 | 25 | 100 | 100 |
| | B (Willamette) | 1.56 | 12.5 | >100 | 100 |
| | C (Nugget) | 3.13 | 12.5 | 100 | 50 |
| | D (Galena) | 3.13 | 25 | 100 | 50 |
| | GC (Saline) | >100 | >100 | >100 | N/A |
| E. faecium (VRE) | A (Magnum) | 25 | 100 | 100 | 100 |
| | B (Willamette) | 25 | 50 | 100 | 100 |
| | C (Nugget) | 25 | 50 | 100 | 100 |
| | D (Galena) | 25 | 50 | 100 | 100 |
| | GC (Saline) | >100 | >100 | >100 | N/A |

*This was the highest concentration of each test article at which the corresponding neutralizer efficacy test (i.e., pre-mixing test article 1:1 with neutralizing broth prior to challenging biofilm) yielded turbidity.
Note:
Neutralizer supplement was non-toxic (i.e., yielded growth) at concentrations as high as 25%, but was only used at a final concentration of 2.5% in neutralizing broth.

TABLE 7

Summary of Quantitative Data. Neutralizer Efficacy Results for S. aureus

| Hop Extract | Conc. (% T:N) | Log10 CFU | Log10 Reduction vs saline |
|---|---|---|---|
| Magnum | 100 | 0.00 | 0.35 |
| | 50 | 2.10 | 4.41 |
| | 25 | 6.10 | 0.12 |
| | 12.5 | 5.50 | 0.57 |
| | 6.25 | 5.45 | 0.53 |
| | 3.13 | 6.06 | 0.03 |
| | 1.56 | 6.20 | −0.23 |
| | SC | 0.00 | 0.00 |
| Willamette | 100 | 0.00 | 0.35 |
| | 50 | 0.00 | 6.51 |
| | 25 | 2.72 | 3.50 |
| | 12.5 | 6.02 | 0.05 |
| | 6.25 | 6.14 | −0.15 |
| | 3.13 | 5.62 | 0.47 |
| | 1.56 | 5.87 | 0.10 |
| | SC | 0.00 | 0.00 |
| Nugget | 100 | 0.00 | 0.35 |
| | 50 | 1.06 | 5.06 |
| | 25 | 4.59 | 1.37 |

TABLE 7-continued

Summary of Quantitative Data. Neutralizer Efficacy Results for S. aureus

| Hop Extract | Conc. (% T:N) | Log10 CFU | Log10 Reduction vs saline |
|---|---|---|---|
| | 12.5 | 5.66 | 0.31 |
| | 6.25 | 5.60 | 0.45 |
| | 3.13 | 5.61 | 0.33 |
| | 1.56 | 5.17 | 0.25 |
| | SC | 1.06 | −1.06 |
| | 100 | 0.00 | 0.35 |
| | 50 | 2.07 | 4.05 |
| Galena | 25 | 5.10 | 0.86 |
| | 12.5 | 5.72 | 0.25 |

TABLE 7-continued

Summary of Quantitative Data. Neutralizer Efficacy Results for S. aureus

| Hop Extract | Conc. (% T:N) | Log10 CFU | Log10 Reduction vs saline |
|---|---|---|---|
| | 6.25 | 5.87 | 0.19 |
| | 3.13 | 5.25 | 0.69 |
| | 1.56 | 5.73 | −0.31 |
| | SC | 1.63 | −1.63 |

Neutralizer supplement was non-toxic (i.e., log reductions <1 relative to the corresponding saline control) at concentrations as high as 12.5%, but was only used at a final concentration of 2.5% in neutralizing broth.

TABLE 8

Neutralizer Efficacy Results for L. monocytogenes.

| Hop Extract | Conc. (% T:N) | Log10 CFU | Log10 Reduction vs saline |
|---|---|---|---|
| Magnum | 100 | 0.00 | 3.35 |
| | 50 | 5.72 | 0.37 |
| | 25 | 5.87 | −0.09 |

TABLE 8-continued

| | | Neutralizer Efficacy Results for *L. monocytogenes.* | |
|---|---|---|---|
| Hop Extract | Conc. (% T:N) | Log10 CFU | Log10 Reduction vs saline |
| | 12.5 | 5.80 | 0.09 |
| | 6.25 | 5.72 | −0.07 |
| | 3.13 | 6.02 | −0.26 |
| | 1.56 | 6.66 | −0.65 |
| | SC | 0.00 | 0.00 |
| Willamette | 100 | 0.00 | 3.35 |
| | 50 | 5.50 | 0.59 |
| | 25 | 5.25 | 0.53 |
| | 12.5 | 6.62 | −0.74 |
| | 6.25 | 6.70 | −1.05 |
| | 3.13 | 5.98 | −0.22 |
| | 1.56 | 5.92 | 0.09 |
| | SC | 0.00 | 0.00 |
| Nugget | 100 | 0.00 | 3.37 |
| | 50 | 5.36 | 0.45 |
| | 25 | 5.36 | 0.68 |
| | 12.5 | 6.06 | −0.14 |
| | 6.25 | 6.02 | −0.10 |
| | 3.13 | 5.72 | 0.11 |
| | 1.56 | 5.87 | −0.01 |
| | SC | 0.00 | 0.00 |
| Galena | 100 | 0.00 | 3.37 |
| | 50 | 5.25 | 0.56 |
| | 25 | 5.87 | 0.18 |
| | 12.5 | 6.28 | −0.36 |
| | 6.25 | 5.62 | 0.30 |
| | 3.13 | 5.62 | 0.21 |
| | 1.56 | 5.72 | 0.14 |
| | SC | 0.00 | 0.00 |

Neutralizer supplement was non-toxic (i.e., log reductions <1 relative to the corresponding saline control) at concentrations as high as 25%, but was only used at a final concentration of 2.5% in neutralizing broth.

TABLE 9

| | | Neutralizer Efficacy Results for *E. faecium* (VRE). | |
|---|---|---|---|
| Hop Extract | Conc. (% T:N) | Log10 CFU | Log10 Reduction vs saline |
| Magnum | 100 | 2.07 | 0.39 |
| | 50 | 4.60 | 0.22 |
| | 25 | 4.32 | 0.16 |
| | 12.5 | 4.72 | −0.29 |
| | 6.25 | 4.92 | −0.09 |
| | 3.13 | 4.98 | −0.27 |
| | 1.56 | 5.54 | −0.83 |
| | SC | 1.06 | −1.06 |
| Willamette | 100 | 2.32 | 0.13 |
| | 50 | 4.44 | 0.38 |
| | 25 | 4.25 | 0.24 |
| | 12.5 | 4.59 | −0.16 |
| | 6.25 | 5.30 | −0.47 |
| | 3.13 | 4.87 | −0.16 |
| | 1.56 | 5.02 | −0.31 |
| | SC | 0.00 | 0.00 |
| Nugget | 100 | 2.20 | 0.51 |
| | 50 | 5.14 | −0.94 |
| | 25 | 4.42 | −0.03 |
| | 12.5 | 4.72 | −0.07 |
| | 6.25 | 4.98 | −0.25 |
| | 3.13 | 5.34 | −0.40 |
| | 1.56 | 5.38 | −0.35 |
| | SC | 0.00 | 0.00 |
| Galena | 100 | 2.03 | 0.68 |
| | 50 | 5.20 | −1.01 |
| | 25 | 5.20 | −0.81 |
| | 12.5 | 4.92 | −0.28 |
| | 6.25 | 5.45 | −0.73 |
| | 3.13 | 5.17 | −0.23 |

TABLE 9-continued

| | | Neutralizer Efficacy Results for *E. faecium* (VRE). | |
|---|---|---|---|
| Hop Extract | Conc. (% T:N) | Log10 CFU | Log10 Reduction vs saline |
| | 1.56 | 5.20 | −0.16 |
| | SC | 0.00 | 0.00 |

Neutralizer supplement was non-toxic (i.e., log reductions <1 relative to the corresponding saline control) at concentrations as high as 25%, but was only used at a final concentration of 2.5% in neutralizing broth.

TABLE 10

| | | Log10 reductions and MBECs for *S. aureus.* | | | |
|---|---|---|---|---|---|
| Hop Extract | Conc. (%) | Mean log10 CFU | SD | Log10 Reduction | P-value |
| Magnum (P1) | 100 | 0.00 | 0.00 | 0.35 | 0.37 |
| | 50 | 0.00 | 0.00 | 6.51 | 0.00 |
| | 25 | 0.35 | 0.61 | 5.87 | 0.00 |
| | 12.5 | 0.35 | 0.61 | 5.72 | 0.00 |
| | 6.25 | 1.02 | 1.77 | 4.96 | 0.01 |
| | 3.13 | 4.42 | 1.04 | 1.67 | 0.05 |
| | 1.56 | 5.39 | 0.44 | 0.58 | 0.09 |
| | SC | 0.00 | 0.00 | 0.00 | 0.00 |
| Willamette (P1) | 100 | 0.00 | 0.00 | 0.35 | 0.37 |
| | 50 | 0.00 | 0.00 | 6.51 | 0.00 |
| | 25 | 0.00 | 0.00 | 6.22 | 0.00 |
| | 12.5 | 0.00 | 0.00 | 6.07 | 0.00 |
| | 6.25 | 0.00 | 0.00 | 5.98 | 0.00 |
| | 3.13 | 1.38 | 1.32 | 4.71 | 0.00 |
| | 1.56 | 1.01 | 0.99 | 4.95 | 0.00 |
| | SC | 0.00 | 0.00 | 0.00 | 0.00 |
| Nugget (P2) | 100 | 0.00 | 0.00 | 0.35 | 0.37 |
| | 50 | 0.00 | 0.00 | 6.12 | 0.00 |
| | 25 | 0.00 | 0.00 | 5.96 | 0.00 |
| | 12.5 | 0.35 | 0.61 | 5.62 | 0.00 |
| | 6.25 | 1.68 | 1.71 | 4.37 | 0.01 |
| | 3.13 | 0.45 | 0.78 | 5.49 | 0.00 |
| | 1.56 | 2.67 | 2.30 | 2.75 | 0.11 |
| | SC | 0.00 | 0.00 | 0.00 | 0.00 |
| Galena (P2) | 100 | 0.00 | 0.00 | 0.35 | 0.37 |
| | 50 | 0.00 | 0.00 | 6.12 | 0.00 |
| | 25 | 0.71 | 0.61 | 5.25 | 0.00 |
| | 12.5 | 1.15 | 0.16 | 4.82 | 0.00 |
| | 6.25 | 0.50 | 0.87 | 5.55 | 0.00 |
| | 3.13 | 2.21 | 2.11 | 3.73 | 0.04 |
| | 1.56 | 5.33 | 0.41 | 0.08 | 0.84 |
| | SC | 0.60 | 1.04 | −0.60 | 0.37 |
| GC (Saline) (P1) | 100 | 0.35 | 0.61 | — | — |
| | 50 | 6.51 | 0.14 | — | — |
| | 25 | 6.22 | 0.16 | — | — |
| | 12.5 | 6.07 | 0.06 | — | — |
| | 6.25 | 5.98 | 0.22 | — | — |
| | 3.13 | 6.09 | 0.21 | — | — |
| | 1.56 | 5.97 | 0.10 | — | — |
| | SC | 0.00 | 0.00 | — | — |
| GC (Saline) (P2) | 100 | 0.35 | 0.61 | — | — |
| | 50 | 6.12 | 0.28 | — | — |
| | 25 | 5.96 | 0.03 | — | — |
| | 12.5 | 5.97 | 0.22 | — | — |
| | 6.25 | 6.05 | 0.10 | — | — |
| | 3.13 | 5.94 | 0.21 | — | — |
| | 1.56 | 5.42 | 0.54 | — | — |
| | SC | 0.00 | 0.00 | — | — |

P1 = plate 1;
P2 = Plate 2.
P-values (relative to corresponding saline controls) determined by 2-tailed, unpaired T-Test.

TABLE 11

Log 10 reductions and MBECs for *L. monocytogenes*.

| Hop Extract | Conc. (%) | Mean log10 CFU | SD | Log10 Reduction | P-value |
|---|---|---|---|---|---|
| Magnum (P1) | 100 | 0.00 | 0.00 | 3.35 | 0.00 |
| | 50 | 4.42 | 0.18 | 1.67 | 0.00 |
| | 25 | 4.39 | 0.14 | 1.38 | 0.00 |
| | 12.5 | 4.47 | 0.22 | 1.42 | 0.00 |
| | 6.25 | 4.71 | 0.18 | 0.94 | 0.00 |
| | 3.13 | 5.83 | 0.33 | −0.07 | 0.77 |
| | 1.56 | 6.37 | 0.34 | −0.35 | 0.16 |
| | SC | 0.00 | 0.00 | 0.00 | 0.00 |
| Willamette (P1) | 100 | 0.00 | 0.00 | 3.35 | 0.00 |
| | 50 | 3.84 | 0.32 | 2.25 | 0.00 |
| | 25 | 4.58 | 0.19 | 1.20 | 0.00 |
| | 12.5 | 5.00 | 0.57 | 0.89 | 0.07 |
| | 6.25 | 4.72 | 0.20 | 0.93 | 0.00 |
| | 3.13 | 5.12 | 0.04 | 0.64 | 0.01 |
| | 1.56 | 6.50 | 0.04 | −0.48 | 0.00 |
| | SC | 0.00 | 0.00 | 0.00 | 0.00 |
| Nugget (P2) | 100 | 0.00 | 0.00 | 3.37 | 0.00 |
| | 50 | 3.13 | 0.09 | 2.69 | 0.00 |
| | 25 | 4.87 | 0.22 | 1.17 | 0.00 |
| | 12.5 | 4.87 | 0.20 | 1.05 | 0.01 |
| | 6.25 | 5.09 | 0.21 | 0.83 | 0.00 |
| | 3.13 | 4.97 | 0.36 | 0.87 | 0.03 |
| | 1.56 | 5.52 | 0.17 | 0.33 | 0.10 |
| | SC | 0.00 | 0.00 | 0.00 | 0.00 |
| Galena (P2) | 100 | 0.00 | 0.00 | 3.37 | 0.00 |
| | 50 | 4.26 | 0.47 | 1.55 | 0.01 |
| | 25 | 5.07 | 0.25 | 0.97 | 0.00 |
| | 12.5 | 5.04 | 0.25 | 0.88 | 0.03 |
| | 6.25 | 4.96 | 0.21 | 0.96 | 0.00 |
| | 3.13 | 5.02 | 0.35 | 0.82 | 0.03 |
| | 1.56 | 6.28 | 0.10 | −0.43 | 0.03 |
| | SC | 0.00 | 0.00 | 0.00 | 0.00 |
| GC (Saline) (P1) | 100 | 3.35 | 0.55 | — | — |
| | 50 | 6.09 | 0.13 | — | — |
| | 25 | 5.78 | 0.21 | — | — |
| | 12.5 | 5.88 | 0.22 | — | — |
| | 6.25 | 5.65 | 0.12 | — | — |
| | 3.13 | 5.76 | 0.24 | — | — |
| | 1.56 | 6.02 | 0.09 | — | — |
| | SC | 0.00 | 0.00 | — | — |
| GC (Saline) (P2) | 100 | 3.37 | 0.41 | — | — |
| | 50 | 5.81 | 0.10 | — | — |
| | 25 | 6.04 | 0.17 | — | — |
| | 12.5 | 5.92 | 0.37 | — | — |
| | 6.25 | 5.92 | 0.05 | — | — |
| | 3.13 | 5.83 | 0.27 | — | — |
| | 1.56 | 5.86 | 0.21 | — | — |
| | SC | 0.00 | 0.00 | — | — |

P1 = plate 1;
P2 = Plate 2.
P-values (relative to corresponding saline controls) determined by 2-tailed T-Test.

TABLE 12

Log 10 reductions and MBECs for *E. faecium* (VRE).

| Hop Extract | Conc. (%) | Mean log10 CFU | SD | Log10 Reduction | P-value |
|---|---|---|---|---|---|
| Magnum (P1) | 100 | 0.00 | 0.00 | 2.46 | 0.00 |
| | 50 | 2.65 | 1.23 | 2.17 | 0.04 |
| | 25 | 3.00 | 1.15 | 1.49 | 0.09 |
| | 12.5 | 3.45 | 0.66 | 0.98 | 0.08 |
| | 6.25 | 3.66 | 0.18 | 1.17 | 0.00 |
| | 3.13 | 3.44 | 0.26 | 1.26 | 0.01 |
| | 1.56 | 4.14 | 1.50 | 0.57 | 0.54 |
| | SC | 0.00 | 0.00 | 0.00 | 0.00 |
| Willamette (P1) | 100 | 0.00 | 0.00 | 2.46 | 0.00 |
| | 50 | 1.33 | 0.47 | 3.49 | 0.00 |
| | 25 | 2.55 | 0.49 | 1.94 | 0.00 |
| | 12.5 | 3.22 | 0.36 | 1.21 | 0.01 |
| | 6.25 | 3.94 | 0.03 | 0.89 | 0.00 |
| | 3.13 | 3.66 | 0.32 | 1.05 | 0.02 |
| | 1.56 | 3.21 | 0.04 | 1.51 | 0.00 |
| | SC | 0.00 | 0.00 | 0.00 | 0.00 |
| Nugget (P2) | 100 | 0.00 | 0.00 | 2.71 | 0.00 |
| | 50 | 2.19 | 0.46 | 2.00 | 0.00 |
| | 25 | 2.58 | 0.25 | 1.81 | 0.00 |
| | 12.5 | 2.63 | 0.39 | 2.02 | 0.00 |
| | 6.25 | 3.92 | 0.75 | 0.81 | 0.14 |
| | 3.13 | 3.50 | 0.51 | 1.44 | 0.01 |
| | 1.56 | 3.61 | 0.78 | 1.43 | 0.04 |
| | SC | 0.00 | 0.00 | 0.00 | 0.00 |
| Galena (P2) | 100 | 0.00 | 0.00 | 2.71 | 0.00 |
| | 50 | 2.43 | 0.81 | 1.76 | 0.02 |
| | 25 | 2.19 | 0.66 | 2.19 | 0.01 |
| | 12.5 | 3.33 | 0.19 | 1.32 | 0.00 |
| | 6.25 | 3.98 | 0.76 | 0.74 | 0.17 |
| | 3.13 | 3.45 | 0.25 | 1.49 | 0.00 |
| | 1.56 | 2.88 | 0.07 | 2.15 | 0.00 |
| | SC | 0.00 | 0.00 | 0.00 | 0.00 |
| GC (Saline) (P1) | 100 | 2.46 | 0.28 | — | — |
| | 50 | 4.82 | 0.30 | — | — |
| | 25 | 4.49 | 0.23 | — | — |
| | 12.5 | 4.43 | 0.27 | — | — |
| | 6.25 | 4.83 | 0.13 | — | — |
| | 3.13 | 4.70 | 0.33 | — | — |
| | 1.56 | 4.71 | 0.09 | — | — |
| | SC | 0.00 | 0.00 | — | — |
| GC (Saline) (P2) | 100 | 2.71 | 0.47 | — | — |
| | 50 | 4.19 | 0.28 | — | — |
| | 25 | 4.39 | 0.16 | — | — |
| | 12.5 | 4.65 | 0.13 | — | — |
| | 6.25 | 4.72 | 0.08 | — | — |
| | 3.13 | 4.94 | 0.15 | — | — |
| | 1.56 | 5.03 | 0.15 | — | — |
| | SC | 0.00 | 0.00 | — | — |

P1 = plate 1;
P2 = Plate 2.
P-values (relative to corresponding saline controls) determined by 2-tailed, unpaired T-Test.

TABLE 13

Summary of Disk Diffusion data

| Disk diffusion | | *B. subtills* | *L. monocetogenes* | MRSA | *S. aureus* | VRE | *S. pneumoniae* | *C. acnes* | *S. pyogenes* | *A. vitis* | *L. lactis* | *L. mesenteroides* |
|---|---|---|---|---|---|---|---|---|---|---|---|---|
| Brewers | mean | 14.3 | 20.2 | 20.7 | 20.7 | 15.4 | 28.7 | 27.9 | 10.4 | | | 12.0 |
| Gold | p value | 0.00 | 0.04 | 0.00 | 0.00 | 0.08* | 0.02 | 0.00 | 0.00 | | | 0.04 |
| Cascade | mean | 16.8 | 21.9 | 23.6 | 22.8 | 16.7 | 30.6 | 30.1 | 10.9 | | | 9.4 |
| | p value | 0.00 | 0.02 | 0.00 | 0.00 | 0.07* | 0.00 | 0.01 | 0.03 | | | 0.02 |
| Cashmere | mean | 18.3 | 19.3 | 23.0 | 22.7 | 16.3 | 31.8 | 31.3 | 11.2 | | | 9.7 |
| | p value | 0.00 | 0.05 | 0.00 | 0.01 | 0.04 | 0.01 | 0.00 | 0.00 | | | 0.03 |
| Centennial | mean | 15.3 | 19.0 | 21.0 | 19.8 | 15.7 | 30.3 | 32.7 | 10.3 | | | 9.1 |
| | p value | 0.00 | 0.04 | 0.00 | 0.00 | 0.09* | 0.01 | 0.01 | 0.01 | | | 0.01 |
| Challenger | mean | 15.6 | 20.2 | 23.8 | 21.8 | 14.3 | 32.2 | 31.1 | 10.3 | | | 9.3 |
| | p value | 0.01 | 0.07 | 0.00 | 0.00 | 0.13* | 0.01 | 0.01 | 0.01 | | | 0.00 |
| Chinook | mean | 14.8 | 19.1 | 21.6 | 19.7 | 14.2 | 25.0 | 28.0 | 9.0 | | | 9.2 |
| | p value | 0.00 | 0.03 | 0.00 | 0.00 | 0.13* | 0.00 | 0.01 | 0.02 | | | 0.02 |

TABLE 13-continued

Summary of Disk Diffusion data

| Disk diffusion | | B. subtilis | L. monocetogenes | MRSA | S. aureus | VRE | S. pneumoniae | C. acnes | S. pyogenes | A. vitis | L. lactis | L. mesenteroides |
|---|---|---|---|---|---|---|---|---|---|---|---|---|
| Hallertau | mean | 17.3 | 22.6 | 24.7 | 22.5 | 17.4 | 29.8 | 32.3 | 10.3 | | | 8.9 |
| | p value | 0.00 | 0.01 | 0.00 | 0.00 | 0.08* | 0.00 | 0.00 | 0.04 | | | 0.01 |
| Magnum | mean | 16.5 | 21.1 | 23.6 | 21.4 | 15.6 | 29.5 | 33.4 | 10.7 | | | 8.9 |
| | p value | 0.00 | 0.02 | 0.00 | 0.00 | 0.11* | 0.00 | 0.00 | 0.00 | | | 0.03 |
| Northern | mean | 14.9 | 20.7 | 23.9 | 19.7 | 17.4 | 29.1 | 33.9 | 11.5 | | | 11.9 |
| Brew | p value | 0.03 | 0.02 | 0.00 | 0.00 | 0.08* | 0.00 | 0.01 | 0.01 | | | 0.01 |
| Nugget | mean | 17.1 | 19.7 | 21.8 | 20.5 | 15.3 | 29.7 | 30.9 | 10.6 | | | 8.4 |
| | p value | 0.00 | 0.03 | 0.00 | 0.01 | 0.11* | 0.01 | 0.00 | 0.00 | | | 0.02 |
| Saaz | mean | 13.2 | 19.8 | 20.1 | 18.5 | 13.1 | 26.0 | 29.1 | 10.0 | | | 9.3 |
| | p value | 0.00 | 0.01 | 0.01 | 0.00 | 0.11* | 0.00 | 0.00 | 0.01 | | | 0.00 |
| Willamette | mean | 17.7 | 20.4 | 23.6 | 20.5 | 17.2 | 29.9 | 33.1 | 10.4 | | | 10.1 |
| | p value | 0.00 | 0.03 | 0.00 | 0.00 | 0.06* | 0.00 | 0.01 | 0.00 | | | 0.01 |
| Crystal | mean | 10.9 | 19.4 | 21.2 | 19.3 | 14.4 | 23.3 | 31.0 | 10.2 | | | 7.8 |
| | p value | 0.07 | 0.03 | 0.00 | 0.00 | 0.10* | 0.00 | 0.02 | 0.02 | | | 0.04 |
| Galena | mean | 18.6 | 22.9 | 24.7 | 22.4 | 16.9 | 31.9 | 35.1 | 12.1 | | | 13.1 |
| | p value | 0.00 | 0.01 | 0.00 | 0.01 | 0.10* | 0.01 | 0.01 | 0.00 | | | 0.00 |
| Wild Hop | mean | 14.5 | 22.0 | 23.4 | 21.4 | 16.1 | 25.8 | 29.0 | 10.0 | | | 8.9 |
| | p value | 0.00 | 0.02 | 0.00 | 0.01 | 0.09* | 0.00 | 0.00 | 0.00 | | | 0.00 |

E. coli, S. typhimurium, G. cerenus showed no inhibition
All numbers represented as mm,
*p-values larger that 0.05 significance.

TABLE 14

Inoculum densities (n = 3) of P. larvae

| O/N culture | Diluted Culture* | Mean Log$_{10}$ CFU/mL | SD | Mean Log$_{10}$ CFU/mL | SD |
|---|---|---|---|---|---|
| 8.19 | 0.43 | 5.42 | | 0.20 | |

*Diluted 1000-fold from the O/N ("overnight") culture; used to inoculate the MBEC devices.

TABLE 15

Summary of Semi-Quantitative Data from the Visual Turbidity Assays
MIC, MBC, and MBEC values for the various test articles are reported
as percentages (where "100%" corresponds to the undiluted test article).

| Organism | Test Article | MIC (%) | MBC (%) | MBEC (%) | Neut. Effective against: (Max. % of test article)** |
|---|---|---|---|---|---|
| P. larvae | A (Magnum) | <1.56 | <1.56 | <1.56 | 1.56 |
| (ATCC 9545) | B (Willamette) | <1.56 | <1.56 | <1.56 | <1.56 |
| | C (Nugget) | <1.56 | <3.13* | <3.13* | <3.13 |
| | D (Galena) | <1.56 | <3.13* | <3.13* | <3.13 |
| | GC (Saline) | 100 | 100 | 100 | N/A |

*In plate 2 (which contained articles C and D), no growth was observed in all of row G (i.e., the 1.56% row), including the saline controls; row G is thus excluded from this analysis, and minimal values are reported as < 3.13%
**This was the highest concentration of each test article at which the corresponding neutralizer efficacy test (i.e., pre-mixing test article 1:1 with neutralizing broth prior to challenging biofilm) yielded turbidity.
Note:
Neutralizing broth was non-toxic (i.e., yielded growth) at concentrations as high as 50% (plate 1) or 100% (plate 2).

TABLE 16

Neutralizer Efficacy Results for P. larvae

| Hop Extract | Conc. (% T:N) | Log$_{10}$ CFU | Log$_{10}$ Reduction vs saline |
|---|---|---|---|
| Magnum | 100.00 | 0.00 | — |
| | 50.00 | 0.00 | 4.02 |
| | 25.00 | 0.00 | 4.85 |
| | 12.5 | 0.00 | 5.18 |
| | 6.25 | 0.00 | 5.59 |

TABLE 16-continued

Neutralizer Efficacy Results for P. larvae

| Hop Extract | Conc. (% T:N) | Log$_{10}$ CFU | Log$_{10}$ Reduction vs saline |
|---|---|---|---|
| | 3.13 | 0.00 | 5.71 |
| | 1.56 | 4.70 | −0.84 |
| | SC | 0.00 | — |
| Willamette | 100.00 | 0.00 | — |
| | 50.00 | 0.00 | 4.02 |

TABLE 16-continued

Neutralizer Efficacy Results for *P. larvae*

| Hop Extract | Conc. (% T:N) | Log$_{10}$ CFU | Log$_{10}$ Reduction vs saline |
|---|---|---|---|
| | 25.00 | 0.00 | 4.85 |
| | 12.5 | 0.00 | 5.18 |
| | 6.25 | 2.48 | 3.11 |
| | 3.13 | 0.00 | 5.71 |
| | 1.56 | 0.00 | 3.86 |
| | SC | 0.00 | — |
| Nugget | 100.00 | 0.00 | — |
| | 50.00 | 0.00 | 4.72 |
| | 25.00 | 0.00 | 4.28 |
| | 12.50 | 0.00 | 5.96 |
| | 6.25 | 0.00 | 5.75 |
| | 3.13 | 0.00 | 5.95 |
| | 1.56 | 0.00 | — |
| | SC | 0.00 | — |
| Galena | 100.00 | 0.00 | — |
| | 50.00 | 0.00 | 4.72 |
| | 25.00 | 0.00 | 4.28 |
| | 12.50 | 0.00 | 5.96 |
| | 6.25 | 0.00 | 5.75 |
| | 3.13 | 0.00 | 5.95 |
| | 1.56 | 0.00 | — |
| | SC | 0.00 | — |

Note:

Neutralizing broth was non-toxic (i.e., log reductions < 1 relative to the corresponding saline control) at concentrations as high as 50% (plate 1) or 100% (plate 2).

TABLE 17

Log 10 reductions and MBECs for *P. larvae*.

| Hop Extract | Conc. (%) | Mean log10 CFU | SD | Log10 Reduction | P-value |
|---|---|---|---|---|---|
| Magnum (P1) | 100 | 0.00 | 0.00 | — | — |
| | 50 | 0.00 | 0.00 | 4.02 | 0.00 |
| | 25 | 0.00 | 0.00 | 4.85 | 0.00 |
| | 12.5 | 0.00 | 0.00 | 5.18 | 0.00 |
| | 6.25 | 0.00 | 0.00 | 5.59 | 0.00 |
| | 3.13 | 0.00 | 0.00 | 5.71 | 0.00 |
| | 1.56 | 0.00 | 0.00 | 3.86 | 0.12 |
| | SC | 0.00 | 0.00 | — | — |

TABLE 17-continued

Log 10 reductions and MBECs for *P. larvae*.

| Hop Extract | Conc. (%) | Mean log10 CFU | SD | Log10 Reduction | P-value |
|---|---|---|---|---|---|
| Willamette (P1) | 100 | 0.00 | 0.00 | — | — |
| | 50 | 0.00 | 0.00 | 4.02 | 0.00 |
| | 25 | 0.00 | 0.00 | 4.85 | 0.00 |
| | 12.5 | 0.00 | 0.00 | 5.18 | 0.00 |
| | 6.25 | 0.00 | 0.00 | 5.59 | 0.00 |
| | 3.13 | 0.00 | 0.00 | 5.71 | 0.00 |
| | 1.56 | 0.00 | 0.00 | 3.86 | 0.12 |
| | SC | 0.00 | 0.00 | — | — |
| Nugget (P2) | 100 | 0.00 | 0.00 | — | — |
| | 50 | 0.00 | 0.00 | 4.72 | 0.00 |
| | 25 | 0.00 | 0.00 | 4.28 | 0.00 |
| | 12.5 | 0.00 | 0.00 | 5.96 | 0.00 |
| | 6.25 | 0.00 | 0.00 | 5.75 | 0.00 |
| | 3.13 | 0.00 | 0.00 | 5.95 | 0.00 |
| | 1.56* | 0.00* | 0.00 | — | — |
| | SC | 0.00 | 0.00 | — | — |
| Galena (P2) | 100 | 0.00 | 0.00 | — | — |
| | 50 | 0.00 | 0.00 | 4.72 | 0.00 |
| | 25 | 0.00 | 0.00 | 4.28 | 0.00 |
| | 12.5 | 0.00 | 0.00 | 5.96 | 0.00 |
| | 6.25 | 0.00 | 0.00 | 5.75 | 0.00 |
| | 3.13 | 0.00 | 0.00 | 5.95 | 0.00 |
| | 1.56* | 0.00* | 0.00 | — | — |
| | SC | 0.00 | 0.00 | — | — |
| GC (Saline) (P1) | 100 | 0.00 | 0.00 | — | — |
| | 50 | 4.02 | 0.08 | — | — |
| | 25 | 4.85 | 0.27 | — | — |
| | 12.5 | 5.18 | 0.20 | — | — |
| | 6.25 | 5.59 | 0.40 | — | — |
| | 3.13 | 5.71 | 0.24 | — | — |
| | 1.56 | 3.86 | 3.35 | — | — |
| | SC | 0.00 | 0.00 | — | — |
| GC (Saline) (P2) | 100 | 0.00 | 0.00 | — | — |
| | 50 | 4.72 | 0.06 | — | — |
| | 25 | 4.28 | 0.27 | — | — |
| | 12.5 | 5.96 | 0.08 | — | — |
| | 6.25 | 5.75 | 0.16 | — | — |
| | 3.13 | 5.95 | 0.16 | — | — |
| | 1.56* | 0.00* | 0.00 | — | — |
| | SC | 0.00 | 0.00 | — | — |

P1 = plate 1;

P2 = Plate 2; P-values (relative to corresponding saline controls) were determined by 2-tailed, unpaired T-Test.

TABLE 18

Summary of Turbidity Assays and Plate count assays

| Organism | Test Article | Turbidity Assay | | | Quantitative (Plate Count) Assay | | | |
|---|---|---|---|---|---|---|---|---|
| | | MIC (%) | MBC (%) | MBEC (%) | MBEC (%)[a] | Log10 Reduction[b] | P (vs GC) | % Reduction |
| *P. larvae* | A (Magnum) | <1.56 | <1.56 | <1.56 | <1.56 | 3.86 | 0.12 | 99.9862 |
| (ATCC 9545) | B (Willamette) | <1.56 | <1.56 | <1.56 | <1.56 | 3.86 | 0.12 | 99.9862 |
| | C (Nugget) | <1.56 | <3.13* | <3.13* | <3.13* | 5.95 | 0.00 | 99.9999 |
| | D (Galena) | <1.56 | <3.13* | <3.13* | <3.13* | 5.95 | 0.00 | 99.9999 |
| | GC (Saline) | 100 | 100 | 100 | 100 | — | — | — |

[a]This was the lowest concentration yielding >3 log10 reduction.

[b]These log10 CFU reductions represent the maximum achievable reduction (i.e., zero colonies from hops- treated biofilms; log reduction was limited by the density of the saline-treated growth controls). Note also that articles A and B achieved a maximum log reduction of 5.71 log10 at 3.13%.

*In plate 2 (which contained articles C and D), no growth was observed in all of row G (i.e., the 1.56% row), including the saline controls; row G is thus excluded from this analysis, and minimal values are reported as <3.13%.

TABLE 19

Summary: Summary of MIC, MBIC and MBEC Assays

| Organism | Test Article | MIC (%) | MBC (%) | MBEC (%) | Neut. Effective against: (Max. % of test article)** |
|---|---|---|---|---|---|
| *P. larvae* (ATCC 9545) | A (Magnum) | <1.56 | <1.56 | <1.56 | 1.56 |
| | B (Willamette) | <1.56 | <1.56 | <1.56 | <1.56 |
| | C (Nugget) | <1.56 | <3.13* | <3.13* | <3.13 |
| | D (Galena) | <1.56 | <3.13* | <3.13* | <3.13 |
| | GC (Saline) | 100 | 100 | 100 | N/A |

* In plate 2 (which contained articles C and D), no growth was observed in all of row G (i.e., the 1.56% row), including the saline controls; row G is thus excluded from this analysis, and minimal values are reported as <3.13%
** This was the highest concentration of each test article at which the corresponding neutralizer efficacy test (i.e., pre-mixing test article 1:1 with neutralizing broth prior to challenging biofilm) yielded turbidity.
Note:
Neutralizing broth was non-toxic (i.e., yielded growth) at concentrations as high as 50% (plate 1) or 100% (plate 2).

TABLE 20

Summary of Spore Data

| Hop Extract | Concentration | CFU/mL | Log10 CFU/mL ± SD | P-value (vs GC) | Log10 R | % Reduction |
|---|---|---|---|---|---|---|
| A (Magnum) | 100% | 0.00 | 0.00 ± 0.00 | 0.0000 | 3.35 | 99.96 |
| | 10% | 0.00 | 0.00 ± 0.00 | 0.0000 | 3.35 | 99.96 |
| | 1% | $1.17 \times 10^3$ | 2.16 ± 1.87 | 0.3338 | 1.19 | 93.50 |
| | Saline (GC) | $2.23 \times 10^3$ | 3.35 ± 0.02 | — | — | — |
| B (Willamette) | 100% | 0.00 | 0.00 ± 0.00 | 0.0000 | 3.50 | 99.97 |
| | 10% | 0.00 | 0.00 ± 0.00 | 0.0000 | 3.50 | 99.97 |
| | 1% | 0.00 | 0.00 ± 0.00 | 0.0000 | 3.50 | 99.97 |
| | Saline (GC) | $3.23 \times 10^3$ | 3.50 ± 0.14 | — | — | — |
| C (Nugget) | 100% | 0.00 | 0.00 ± 0.00 | 0.0000 | 3.71 | 99.98 |
| | 10% | 0.00 | 0.00 ± 0.00 | 0.0000 | 3.71 | 99.98 |
| | 1% | 0.00 | 0.00 ± 0.00 | 0.0000 | 3.71 | 99.98 |
| | Saline (GC) | $5.33 \times 10^3$ | 3.71 ± 0.15 | — | — | — |
| D (Gelena) | 100% | 0.00 | 0.00 ± 0.00 | 0.0000 | 3.63 | 99.98 |
| | 10% | 0.00 | 0.00 ± 0.00 | 0.0000 | 3.63 | 99.98 |
| | 1% | $1.67 \times 10^3$ | 0.57 ± 0.99 | 0.0060 | 3.06 | 99.91 |
| | Saline (GC) | $4.33 \times 10^3$ | 3.63 ± 0.13 | — | — | — |

Note:
P-values were determined with an unpaired, 2-tailed T-test.

TABLE 21

Relative percentage of total oil

| COMPOUND | W1 | N1 | G1 | M1 |
|---|---|---|---|---|
| 2-udecanone | 0% | 1.86% | 0% | 0% |
| a-pinene | 1.71% | 1.43% | 2.02% | 2.26% |
| B-ionone | 0.0% | 0% | 1.23% | 0% |
| b-pinene | 1.36% | 3.72% | 0.52% | 2.59% |
| Caryophyllene | 3.16% | 2.12% | 3.46% | 5.98% |
| Caryophyllene oxide | 1.14% | 1.06% | 0% | 2.92% |
| Citral | 0% | 0% | 0.27% | 0% |
| Citronellene | 0.66% | 1.14% | 1.16% | 2.79% |
| Citronellol | 0% | 0% | 0% | 0% |
| Farnesene | 0.75% | 1.52% | 0% | 1.26% |
| Geraniol | 0.48% | 0% | 2.94% | 6.78% |
| Geranyl acetate 1 | 0.25% | 0% | 0% | 0% |
| Geranyl acetate 2 | 0.0% | 0% | 0% | 0% |
| Humulene | 8.60% | 6.27% | 6.23% | 14.68% |
| Limonene | 0% | 0% | 0.60% | 2.79% |
| Linalool | 0.44% | 3.61% | 0.65% | 6.84% |
| Methyl heptanoate | 1.05% | 0.43% | 2.75% | 6.98% |
| Methyl laurate | 0% | 0% | 0% | 0% |
| Methyl octanoate | 0.22% | 0% | 0.44% | 0% |
| Methyl | 1.10% | 0.40% | 0% | 2.99% |

TABLE 21-continued

Relative percentage of total oil

| COMPOUND | W1 | N1 | G1 | M1 |
|---|---|---|---|---|
| thiohexanoate | | | | |
| Myrcene | 5.75% | 10.93% | 9.81% | 24.58% |
| Nerol | 0.70% | 0.57% | 0.67% | 1.79% |
| Nerolidol 1 | 0% | 0.92% | 0% | 19.80% |
| Nerolidol 2 | 100% | 100% | 100% | 100% |
| Ocimene | 1.01% | 0% | 0.63% | 0% |
| Terpinolene | 0.88% | 0.52% | 0.28% | 7.77% |

TABLE 22

ACID PERCENTAGES

| Acid | W1 | N1 | G1 | M1 |
|---|---|---|---|---|
| Total iso-alpha | 1.10% | 1.60% | 2.50% | 1.20% |
| Iso cohumulone | 0.45% | 0.59% | 1.10% | 0.99% |
| Iso-humulone | 0.38% | 0.54% | 0.50% | 0.21% |

TABLE 22-continued

| ACID PERCENTAGES | | | | |
|---|---|---|---|---|
| Acid | W1 | N1 | G1 | M1 |
| Iso-adhumulone | 0.22% | 0.47% | 0.94% | ND |
| Alpha | 5.40% | 4.50% | 5.20% | 4.90% |
| Beta | 3.70% | 2.70% | 5.40% | 1.70% |
| Cohumulone | 30.10% | 31.90% | 39.0% | 45.90% |
| Colupulone | 47.40% | 50.90% | 60.60% | 55.60% |

TABLE 23

| Varroa spore Efficacy | | | |
|---|---|---|---|
| Treatment | Replicate | Trial 1 % Mortality | Trail 2 % Mortality |
| 10% | 1 | 60 | 70 |
| 10% | 2 | 40 | 50 |
| 10% | 3 | 30 | 50 |

TABLE 23-continued

| Varroa spore Efficacy | | | |
|---|---|---|---|
| Treatment | Replicate | Trial 1 % Mortality | Trail 2 % Mortality |
| Zero (Control) | 1 | 0 | 20 |
| 25% | 1 | 30 | 30 |
| 25% | 2 | 20 | 30 |
| 25% | 3 | 70 | 30 |
| Zero (Control) | 2 | 20 | 10 |
| 50% | 1 | 50 | 60 |
| 50% | 2 | 80 | 60 |
| 50% | 3 | 50 | 20 |
| Zero (Control) | 3 | 0 | 20 |
| 100% | 1 | 50 | 60 |
| 100% | 2 | 80 | 80 |
| 100% | 3 | 50 | 40 |
| Zero (Control) | 4 | 60 | 60 |
| 200% | 1 | 40 | 100 |
| 200% | 2 | 30 | 80 |
| 200% | 3 | 30 | 50 |
| Zero (Control) | 5 | 100 | 30 |

TABLE 24

| *M. plutonius* | | Turbidity Assay | | | Quantitative (Plate Count) Assay | | | |
|---|---|---|---|---|---|---|---|---|
| Organism | Test Article | MIC (%) | MBC (%) | MBEC (%) | MBEC (%)[a] | Log10 reduction[b] | P (vs GC) | % Reduction |
| *M. plutonius* | NRCS-019 | 10 | 10 | >100 | >100 | 0.40 | 0.70 | 60.1893 |
| (ATCC 35311) | NRCS-014 | 10 | 10 | 100 | >100 | 1.39 | 0.17 | 95.9262 |
| | GC (Saline) | 100 | >100 | >100 | N/A | N/A | N/A | N/A |

The invention claimed is:

1. A method of treating a microbially contaminated hospital or care home surface comprising:

applying an effective amount of a disinfectant composition to the microbially contaminated hospital or care home surface selected from the group consisting of a floor, a countertop or a curtain, the active ingredient of the disinfectant composition prepared by a method comprising:

grinding a quantity of hop cones from hop plants, suspending the ground hop cones in a solution consisting of water, thereby providing forming an aqueous suspension;

boiling the aqueous suspension for at least about 15, 20 or 30 minutes, and recovering the supernatant, thereby providing a boiling water hop extract;

said disinfectant composition arresting microbial growth on the microbially contaminated hospital or care home surface, wherein the microbial growth is from contamination by a bacterium selected from the group consisting of: *Staphylococcus aureus, Enterococcus faecium, Listeria monocytogenes*, Methicillin-Resistant *Staphylococcus aureus* (MRSA) and *Streptococcus pneumonia* and wherein the effective amount yields at least a $\log_{10}$ biofilm reduction in colony forming units of the bacterium relative to a saline control.

2. The method according to claim 1 wherein the hop plant is selected from the group consisting of Brewers Gold; Cascade; Cashmere; Centennial; Challenger; Chinook; Crystal; Galena; Hallertau; Magnum; Northern Brew; Nugget; Saaz; Wild Manitoba hop; Columbus; Nelson Sauvin; Santiam and Willamette.

3. A method of treating a Gram-positive bacterial skin infection in a patient in need of such treatment comprising administering an effective amount of a boiling water hop extract prepared by:

grinding a quantity of hop cones from hop plants, suspending the ground hop cones in a solution consisting of water, thereby providing forming an aqueous suspension;

boiling the aqueous suspension for at least about 15, 20 or 30 minutes, recovering the supernatant, thereby providing the boiling water hop extract, to a person who is suspected of having or who has been diagnosed with a Gram-positive bacterial skin infection, wherein the Gram-positive bacteria is selected from the group consisting of *Cutibacterium acnes, S. aureus*, MRSA *Bacillus subtilis*, Vancomycin-Resistant *Enterococcus faecium* (VRE) and *L. monocytogenes*, and wherein the effective amount yields at least a $\log_{10}$ biofilm reduction in colony forming units of the bacterium relative to a saline control.

4. The method according to claim 3 wherein the hop plant is selected from the group consisting of Brewers Gold; Cascade; Cashmere; Centennial; Challenger; Chinook; Crystal; Galena; Hallertau; Magnum; Northern Brew; Nugget; Saaz; Wild Manitoba hop; Columbus; Nelson Sauvin; Santiam and Willamette.

5. A method of eradicating a biofilm produced by a Gram-positive bacteria comprising applying an effective amount of a disinfectant composition to a microbially contaminated surface comprising a Gram-positive bacteria biofilm, the active ingredient of the disinfectant composition prepared by a method comprising:

grinding a quantity of hop cones from hop plants, suspending the ground hop cones in a solution consisting of water, thereby providing forming an aqueous suspension;

boiling the aqueous suspension for at least about 15, 20 or 30 minutes, and recovering the supernatant, thereby providing a boiling water hop extract;

said disinfectant composition eradicating the biofilm on the microbially contaminated surface, wherein the biofilm is produced by a Gram-positive bacterium selected from the group consisting of: *S. aureus, E. faecium, L. monocytogenes*, MRSA, VRE and *S. pneumonia* and wherein the effective amount yields at least a log10 biofilm reduction in colony forming units of the bacterium relative to a saline control.

6. The method according to claim 5 wherein the hop plant is selected from the group consisting of Brewers Gold; Cascade; Cashmere; Centennial; Challenger; Chinook; Crystal; Galena; Hallertau; Magnum; Northern Brew; Nugget; Saaz; Wild Manitoba hop; Columbus; Nelson Sauvin; Santiam and Willamette.

* * * * *